United States Patent [19]

Halenbeck et al.

[11] Patent Number: 5,830,684

[45] Date of Patent: Nov. 3, 1998

[54] NATIVE TYPE II GAP, METHODS FOR PURIFYING VARIOUS GAPS AND USES OF GAPS TO DIAGNOSE CANCER

[75] Inventors: Robert Halenbeck, San Rafael; Kirston Koths, El Cerrito; Francis P. McCormick, Berkeley; Bonnee Rubinfeld, Danville, all of Calif.; Edward C. O'Rourke, Princeton, N.J.; Robin Clark; Gail L. Wong, both of Oakland, Calif.; George Martin, Berkeley, Calif.

[73] Assignee: Chiron Corporation, Emeryville, Calif.

[21] Appl. No.: 624,299

[22] Filed: Dec. 7, 1990

Related U.S. Application Data

[63] Continuation-in-part of Ser. No. 260,807, Oct. 21, 1988, abandoned, which is a continuation-in-part of Ser. No. 230,761, Aug. 10, 1988, abandoned.

[51] Int. Cl.$^6$ .............................. C12P 21/02; C07K 14/47
[52] U.S. Cl. ........................ 435/69.1; 435/69.2; 530/350
[58] Field of Search ............................. 435/69.1; 530/350

[56] References Cited

U.S. PATENT DOCUMENTS 5,104,975  4/1992  McCormick et al. .................. 530/350

OTHER PUBLICATIONS

Lehninger (1975), Biochemistry, Second Ed., (Worth Publishers, New York), pp. 157–172.
Luckow et al. (1988), Bio/Technology 6: 47–55.
Record et al. (1985), Biochim. Biophys. Acta 819: 1–9.
Suggs et al. (1981), Proc. Natl. Acad. Sci. USA, 78(11): 6613–6617.
Weaver et al. (1989), Genetics (Wm. C. Brown Publishers, Dubuque, Iowa), pp. 451–457.
Trahey et al. (Oct. 1987), Science 238 : 542–545.
Jacobs et al. (Feb. 1985), Nature 313: 806–810.
Trahey et al. (Dec. 1988), Science 242 : 1697–1700.

*Primary Examiner*—Nancy Degen
*Attorney, Agent, or Firm*—Marshall, O'Toole et al.; Robert P. Blackburn

[57] ABSTRACT

Native Type II GAP (GTPase activating protein), its uses in cancer diagnosis, and methods for obtaining and purifying native and recombinant Types I and II GAPs are described.

7 Claims, 17 Drawing Sheets

FIG. 3

ILE MET PRO GLU GLU GLU TYR SER GLU PHE LYS

```
ATC ATG CCC GAG CAG GAG TAC TCC GAG TTC AAG
 T       A   AGA  A    T   T   A    T   A
 A       T                A
         G                G
                         AGC
                          T
```

FIG. 4

Ile MET Pro Glu Glu Glu Tyr Ser Glu Phe Lys

GW13 5'ATC ATG CCT GAG CAG GAG TAC TCT GAG TTC AAG'3

GW15 5'ATC ATG CCT GAG CAG GAG TAC AGT GAG TTC AAG'3

GW17 5'ATC ATG CCT GAG GAG GAG TAC TCT GAG TTC AAG'3

GW19 5'ATC ATG CCT GAG GAG GAG TAC AGT GAG TTC AAG'3

FIG. 5A

```
681  ACCATTTAGGATTATTGCTATGTGTGGAGATTACTACATTGGTGCAAGACGTTTTCTTCACTCTCAGACCTAATAGGTTATTACAGTCATGTTTCTTG  780
229    H  F  R  I  I  A  M  C  G  D  Y  Y  I  G  G  R  R  F  S  S  L  S  D  L  I  G  Y  Y  S  H  V  S  C   261

781  TTTGCTTAAAGGAGAAAATTACTTTACCCAGTTGCACCACCAGAGCCAGTAGAAGATAGAAGGCGTGTACGAGCTATTCTACCTTACACAAAGTACCA  880
262    L  L  K  G  E  K  L  L  Y  P  V  A  P  P  E  P  V  E  D  R  R  R  V  R  A  I  L  P  Y  T  K  V  P   294

881  GACACTGATGAAATAAGTTTCTTAAAAGGAGATATGTTCATTGTTCATAATGAATTAGAAGATGGATGTGGGTTACAAATTTAAGAACAGATGAAC   980
295    D  T  D  E  I  S  F  L  K  G  D  M  F  I  V  H  N  E  L  E  D  G  W  M  W  V  T  N  L  R  T  D  E  Q   328

981  AAGGCCTTATTGTTGAAGACCTAGTAGAAGAGGTGGGCCGGGAAGAAGATCCACATGAAGGAAAAATATGGTTCCATGGAAGATTCCAAACAGGAAGC  1080
329    G  L  I  V  E  D  L  V  E  E  V  G  R  E  E  D  P  H  E  G  K  I  W  F  H  G  K  I  S  K  Q  E  A   361

1081 TTATAATTTACTAATGACAGTTGGTCAAGTCTGCAGTTTTCTTGTGAGGCCCTCAGTTGTCAGGCCCTCAGATAATACTCCTGGCGATTATTCACTTTATTCCGGACATTGAA  1180
362    Y  N  L  L  M  T  V  G  Q  V  C  S  F  L  V  R  P  S  D  N  T  P  G  D  Y  S  L  Y  F  R  T  N  E   394
                                                             A                                              S

1181 AATATTCAGCGATTTAAATATGTCCAACGCCAAACATCAGTTTATGATGGAGGTCGGTATTATAACAGCATTGGGACATCATAGATCACTATCGAA  1280
395    N  I  Q  R  F  K  I  C  P  T  P  N  N  Q  F  M  W  G  G  R  Y  Y  N  S  I  G  D  I  D  H  Y  R  K   428

1281 AAGAACAGATTGTTGAAGGATATTATCTTAAGGAACCTGTACCAATGCAGGATCAAGAACAAGTACTCAATGACACAGTGGATGGCAAGGAAATCTATAA  1380
429    E  Q  I  V  E  G  Y  Y  L  K  E  P  V  P  M  Q  D  Q  E  Q  V  L  N  D  T  V  D  G  K  E  I  Y  N   461
                                                                                     A

1381 TACCATCCGTCGTAAAACAAAGGATGCCTTTTATAAAAACATTGTTAAGAAGGTTATCTTCTGAAAAAGGGCAAAGGAAAACTTGGAAAATTTATAT  1480
462    T  I  R  R  K  T  K  D  A  F  Y  K  N  I  V  K  K  G  Y  L  L  K  K  G  K  R  W  K  N  L  Y   494

1481 TTTATCTTAGAGGGTAGTGATGCCCAACTTATTTATTTTGAAAGCGAAAAACGAGCTACCAAACCAAAGGATTAATAGATCTCAGTGATGTTCTGTGT  1580
495    F  I  L  E  G  S  D  A  Q  L  I  Y  F  F  E  S  E  K  R  A  T  K  P  K  G  L  I  D  L  S  V  C  S  V  Y   528

1581 ATGTCGTTCATGATAGTCTCTTGGCAGGCCAAACTGTTTCAGATAGTCAGCACTTAGTGAAGAACATTACATCTTTACTTTGCAGGAGAAAC  1680
529    V  V  H  D  S  L  F  G  R  P  N  C  F  Q  I  V  V  Q  H  F  S  E  E  H  Y  I  F  Y  F  A  G  E  T   561
```

FIG. 5B

```
1681  TCCAGAACAAGCAGAGGATTGGATGAAAGGTCTGCAGGCATTTGCAATTTACGAAAAGTAGTCCAGGGACATCCAATAAACGCCTTGTCAGGTCAGC  1780
 562   P  E  Q  A  E  D  W  M  K  G  L  Q  A  F  C  N  L  R  K  S  S  P  G  T  S  N  K  R  L  R  Q  V  S   594

1781  AGCCTGTTTTACATATTGAAGAAGCCCATAAACTCCCAGTAAAACATTTTACTAATCCATATTGTAACATCTACCTGAATAGTGTCCAAGTAGCAAAA  1880
 595   S  L  [V]  L  H  I  E  E  A  H  K  L  P  V  K  H  F  T  N  P  Y  C  N  I  Y  L  N  S  V  Q  V  A  K  T   628
            [I]                                                                                        ___

1881  CTCATGCAAGGCAAGGGCAAACCAGTATGTCAGAAGAGTTGTCTTTGATGATCTTCCCTGACATCAATAGATTTGAAATAACTCTTAGTAATAA  1980
 629   H  A  R  E  G  Q  N  P  V  W  S  E  E  F  V  F  D  D  L  P  P  D  I  N  R  F  E  I  T  L  S  N  K   661
                              _____

1981  AACAAAGAAAAGCAAAGATCCTGATATCTTATTTATGCGCTGCCAGTTGACCAGGTCCCTGCTGTTCGAGCACGATGAATGGTTTCTGCTCAGCTCC  2080
 662   T  K  K  S  K  D  P  D  I  L  F  M  R  C  Q  L  S  R  L  Q  K  G  H  A  T  D  E  W  F  L  L  S  S   694
       _____

2081  CATATACCATTAAAAGGTATTGAACCAGGGTCCCTGCTGTCGACGCACGATACTCTATGCAAAAATCATCCAGAAGAAGAGTACAGTGAATTTAAAG  2180
 695   H  I  P  L  K  G  I  E  P  G  S  L  R  V  R  A  R  Y  S  M  E  K  I  M  P  E  E  E  Y  S  E  F  K  E   728
                                                         _____

2181  AGCTTATACTGCAAAAGGAACTTCATGTAGTCGTTATGCTTATCCAGCATCCTACTGGCCAGACCGAACATCCGCAGACACTGCTTAGCATCCTTCT  2280
 729   L  I  L  Q  K  E  L  H  V  V  Y  A  L  S  H  V  C  G  Q  D  R  T  L  L  A  S  I  L  L  [R]  I  F  L   761
                                                                                              [K]

2281  TCACGAAAAGCTTGAATCGTTGTTGTGTTATGCACAATAAAGACAGAGAAATGAAGCATGGAAGATGAAGCCACTACCCTATTTCGAGCCAACACTTGCA  2380
 762   H  E  K  L  E  S  L  L  C  T  L  N  D  R  E  I  S  M  E  D  E  A  T  T  L  F  R  A  T  T  L  A   794

2381  AGCACCTTGATGGCAGCAGTATGAAGCTAACTCAAGTTGTTCATCATGCTTGAAAGACTCTATTTAAAGATAATGGAAAGCAAGCAGTCTT  2480
 795   S  T  L  M  E  Q  [Y]  M  K  A  T  A  T  Q  F  V  H  H  A  L  K  D  S  I  L  [K]  I  M  E  S  K  Q  S  C   828
                        [S]                                                         [R]

2481  GTGAGTTAAGTCCATCAAAGTTAGAAAAAAATGAAGATGTGAACACTAATTTAACACACTTTCAGAGGCTTGTGGAGAAAATATTCAT  2580
 829   E  L  S  P  S  K  L  E  K  N  E  D  V  N  T  N  L  [T]  H  L  N  I  L  S  E  L  V  E  K  I  F  M   861
                                                          [A]

2581  GGCTTCAGAAATACTTCCACCGACATTGAGATATATTTATGGGTGTTTACAGAAATCTGTTCAGCATAAGTGGCCTACAAATACCACCATGAGAACAAGA  2680
 862   A  S  E  I  L  P  P  T  L  R  Y  I  Y  G  C  L  Q  K  S  V  Q  H  K  W  P  T  N  T  T  M  R  T  R   894
```

FIG.5C

```
2681  GTGTTAGTGGTTTTGTTTTCTCCGACTCTGCCTGCCATCCTGAATCCACGGATGTTCAATATCATCTCAGATTCTCCATTGCTGCAA  2780
895   V  V  S  G  F  V  F  L  R  L  I  C  P  A  I  L  N  P  R  M  F  N  I  I  S  D  S  P  I  A  A  R   928

2781  GAACACTGATATTAGTGCCTAAATCTGTGCAGAACTTAGCAAATCTTGTGGAATTTGGAGCCCTACATGGAAGGCTGTCATCCATTCATCAA  2880
929   T  L  [I/T] L  V  A  K  S  V  Q  N  L  V  E  F  G  A  K  E  P  Y  M  E  G  V  N  P  F  I  K   961

2881  AAGCAACAAACATCGTATGATCATGTTTTTAGATGAACTTGGGAATGTACCTGAACTTCCGGACACTACAGAGCATTCTAGAACGGACCTGTCCCGTGAT  2980
962   S  N  K  H  R  M  I  M  F  L  D  E  L  G  N  V  P  E  L  P  D  T  T  E  H  S  R  T  D  L  [S/C] R  D   994

2981  TTAGCAGCATTGCATGAGATTTGCCTGCCTCATTCAGATGAACTTCGAACGACTCTCAGTAATGAGCTGGTGCACAGCAGCACGTGTTGAAAAGCTTCTGG  3080
995   L  A  A  L  H  E  I  C  V  A  H  S  D  E  L  R  T  L  S  N  E  R  G  A  Q  Q  H  V  L  K  K  L  L  A   1028

3081  CTATAACAGAACTGCTTCAACAAAAACAAAACCAGTATACAAAAACCAATGATGTCAGGTAGCAGCCTTCGCCCCAGTGTTCTGCATGGATTCAGCATGT  3180
1029  I  T  E  L  L  Q  Q  K  Q  N  Q  Y  T  K  T  N  D  V  R                                               1047

3181  CCAACACATGGTAATTCACTTCAGTTTAAGTCTCCCTTGCTCTTGCCAAAAATAGCACACTTTTCCACATTCCAGTGATGTGAGCTATGCAAACAAA     3280

3281  TCCAAGATTCTGCTGGTGTACAGACCACCTTGTGAATAACTGCCAGCAACCTTGTAAGCTATCTGTGCAGGATATATTGCACTATTCCACATGAATCAATCATCTTAACAACCTC  3380

3381  TCACCCTTGGTGTGTGTCTCTTAGAGAAAGAACTATGAAATCAACTGACAAGAAACACATTCTTATTGACAATGTGTATAACTGTAGACACTGTTCTAC  3480

3481  AAAGTTTGCTGTCTCCTGATTAGGAATATGACCATTGTCAAAGACTGTATTCTCTTGCTGAACTGTATTAGATCTCATAATGATCTATTGCTCATCAGCTTTATTTGTTCATTATAATAGGAACAATCTTTG  3580

3581  TGTAACTACTTCCTGATTAGGAATATGACCATTGTCAAAGACTGTATTCTCTTGCTGAACTGTGTGAACAAATATATAGAACTTTGTTAAATGTTACAAGTAAATAGTTTGAATTCAGTAAATATATT  3680

3681  CTGTATACTTTAAAAAATACTCTGCTATTTCTGTCAAAGACTGTATTCAACCATTTTTATAGACTACCAATTCTTTTAAGTTAACTAGAATGCTTTGTTAAAAGTTATTTGTT  3780

3781  TACGACTTATATTTGTTGAATCAATGCCATGTTACCCATTCAACCAACAACCTATCAACCTATCAAGTTATCACTACTCACTGCACTGTGTATGTCGTGATATT  3880

3881  GGTGTGTGTATTGATCAATGCTACCCCTTTGATTATTACTTCCTGTATGTGTATTTTTGTCAAGTATTCCACTGTAAGTTAAGTTATTTGT  3980

3981  CATTATTTGTGCTACCCCTTTGATTATTACTTCCTGTATGTGTATTTTTGTCAAGTATTCACTGTAAGTTAAGTTATTTGT            4080

4081  TAGTTCAACTGTATAGTATAGTTTATTACTTCTCGTATGTATTTTTGTCAAGTATTCACAAGGTAAGTTAAATAAAACCAAGGATATCTTGCAAAAAA  4180

4181  AAAAAAA  4187
```

FIG.5D

Orientation of polylinker in pAcC6, pAcC8 :

```
BamHI        Sac I      Bgl II    Eco RI          Sma I
GATCCACCATGGAGCTCGAGATCTAGAATTCTGCAGCCCGGGTACCGATC
     Nco I        Xho I     Xba I       Pst I        Kpn I
```

Orientation of polylinker in pAcC7, pAcC9, and pAcC12 :

```
       Sma I              Eco RI     Bgl II     Sac I          BamHI
GATCGGTACCCGGGCTGCAGAATTCTAGATCTCGAGCTCCATGGTGGATC
     Kpn I        Pst I        Xba I      Xho I         Nco I
```

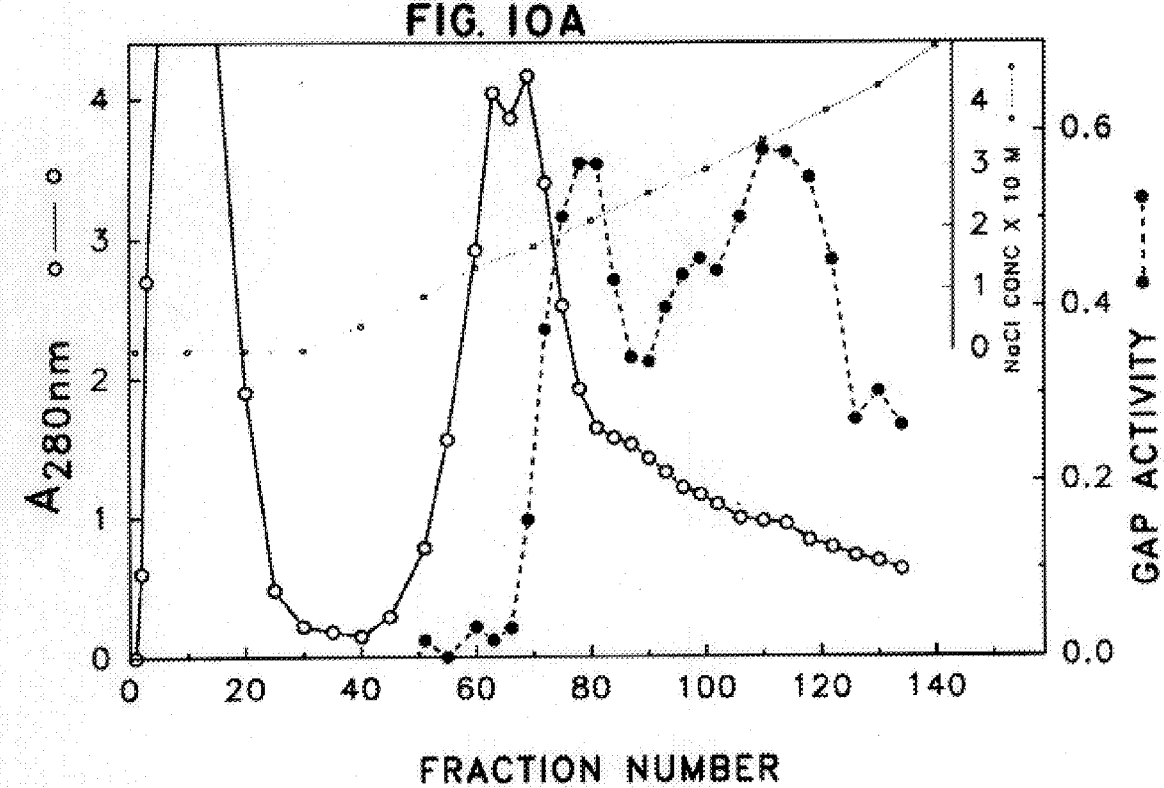
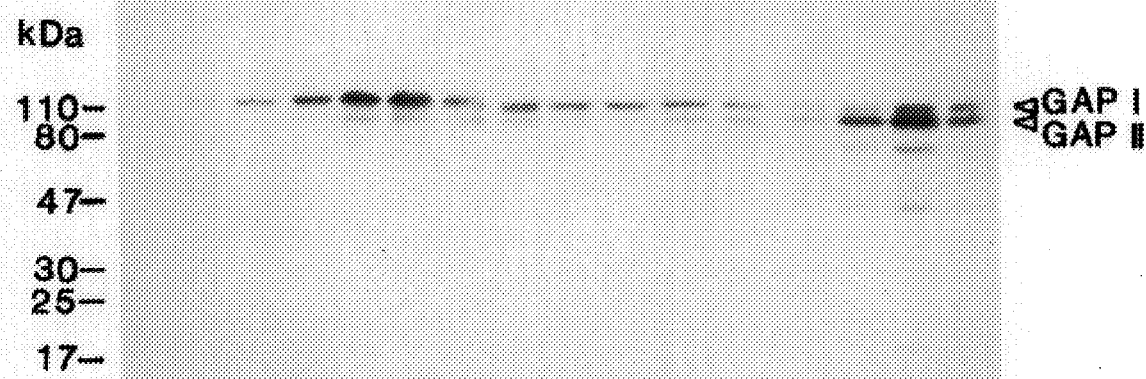

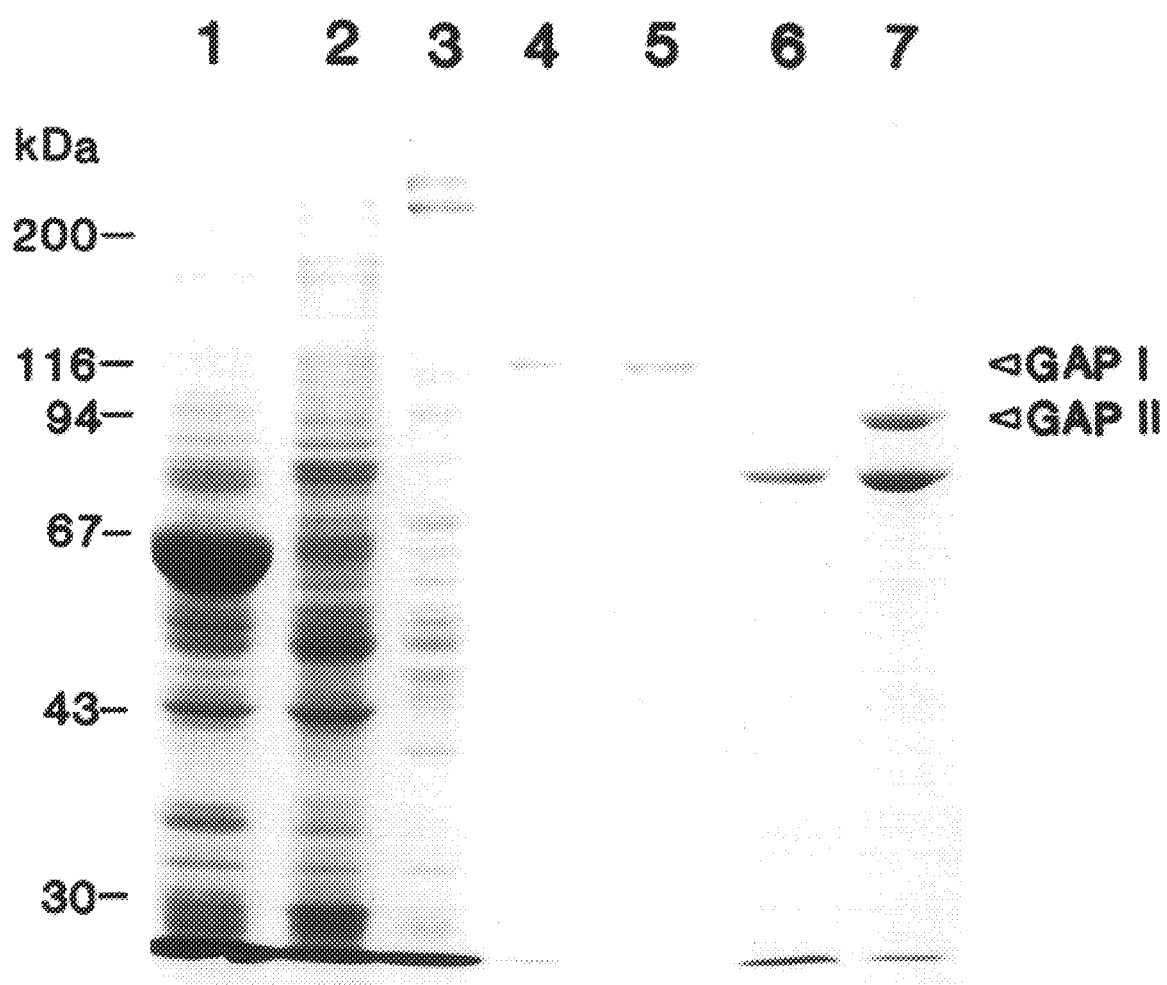

FIG. 12

PREDICTED TYPE I GAP
N-TERMINAL SEQUENCE

MET MET ALA ALA......THR ASN GLN TRP TYR HIS GLY...GLN...
 1   2   3   4       178 179 180 181 182 183 184    197

SEQUENCE DETECTED
FOR TYPE II GAP

MET LYS GLY TRP TYR HIS GLY...GLN
 1   2   3   4   5   6   7     20

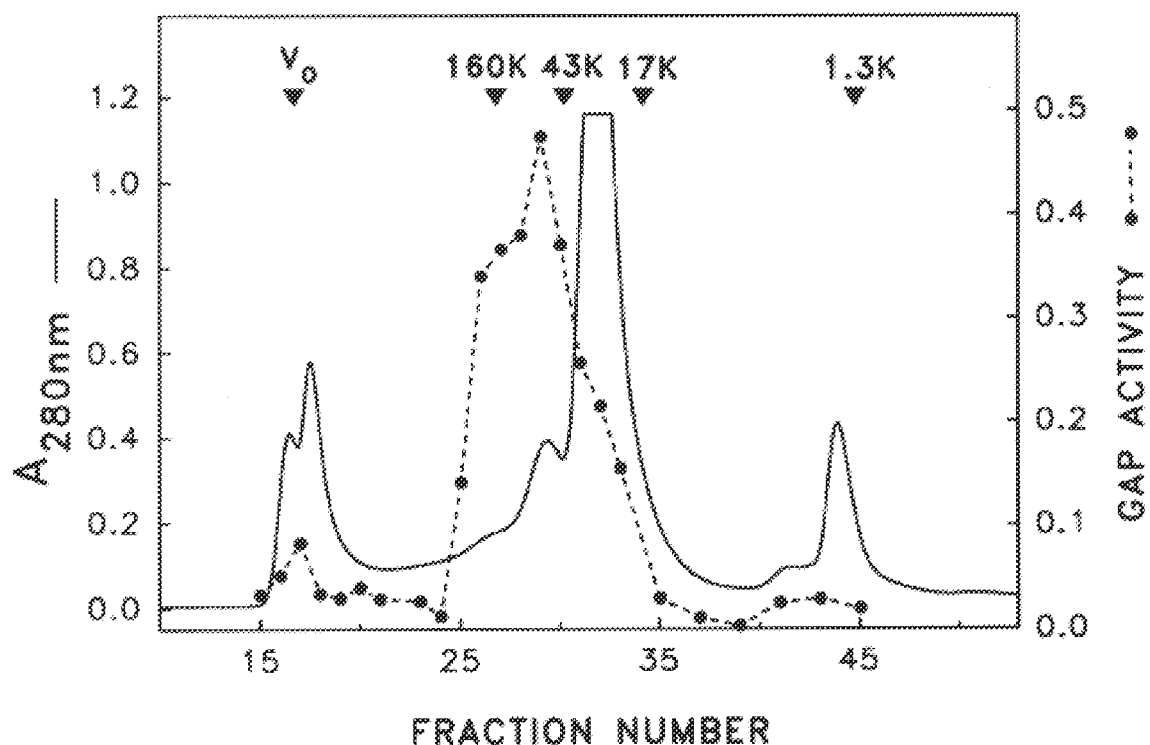

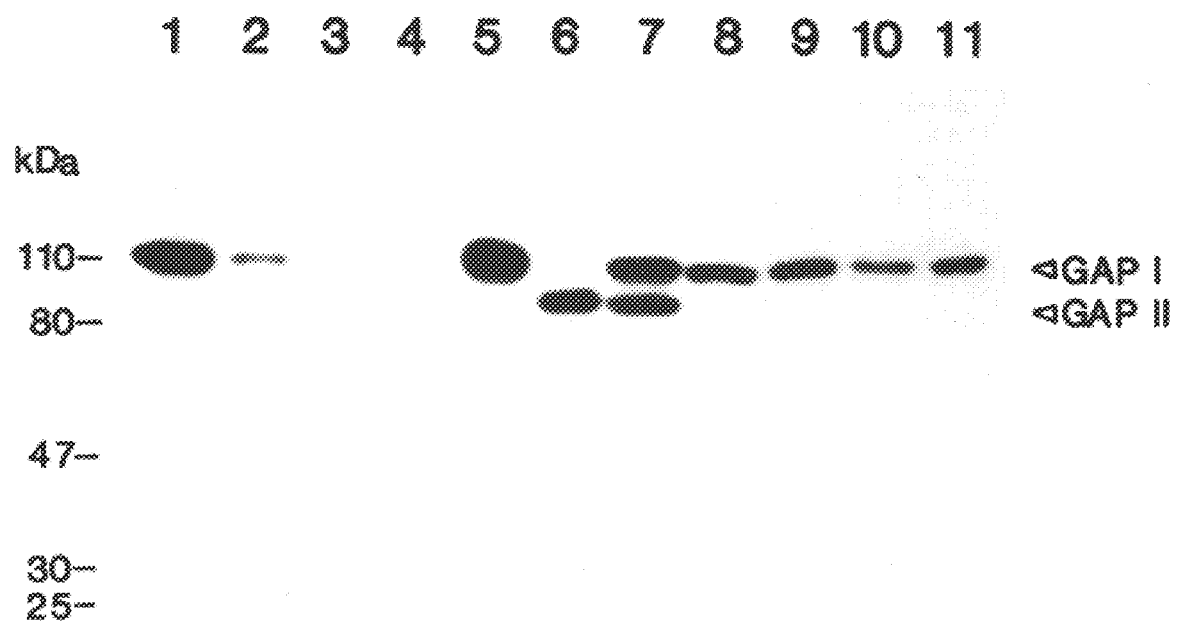

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Asp  Leu  Val  Arg  Gln  Ile  Asn  Arg  Lys  Thr  Pro  Val  Glu  Lys  Lys
 1              5                        10                            15
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Cys  Pro  Pro  Pro  Val  Lys  Lys  Lys  Arg  Lys  Arg  Lys
 1              5                        10
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Asn  Val  Phe  Asp  Glu  Ala  Ile  Leu  Ala  Ala  Leu  Glu  Pro  Pro  Glu  Pro
 1              5                        10                            15
Lys
```

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Phe  Gly  Val  Ser  Thr  Lys  Leu  Pro  Phe  Thr  Trp  Asp  Xaa  Ala  Gln  Gln
 1              5                        10                            15
Leu
```

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Ile Ala Ser Asn Phe Leu Pro Ala Tyr Ile Val Val Gln Ala Asn
1               5                   10                  15
Pro Gly Thr Glu Pro Pro Ala Tyr Lys
                20              25
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Ile Ala Ser Asn Phe Leu Ser Ala Tyr Val Val Val Gln Ala Glu Gly
1               5                   10                  15
Gly Gly Pro Asp Gly Xaa Leu Tyr Lys Val
                20              25
```

( 2 ) INFORMATION FOR SEQ ID NO:7:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGGGGCTCTG TGCCAGGGTT CTCAGCCTGC ACCACAATGT AGGC    44

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GGTTGCACTC GAGCTTCACC TTGGT    25

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

AAGCACTTTC TCGGCAAGGA 20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GAACCGATCC ACATTGACGT 20

( 2 ) INFORMATION FOR SEQ ID NO:11:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

AACTTTGCCA TCTGGACAAC ATTAGGGAAC TCGGTGAGGC AGGAGATGG 49

( 2 ) INFORMATION FOR SEQ ID NO:12:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

GGTACCCGGG CTGCAGAATT CTAGATCTCG AGCTCCATGG TGGATCC 47

( 2 ) INFORMATION FOR SEQ ID NO:13:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GTACCAGATC TGCAGAATTC TAGAGGATCC TGATCAGCTA GAGAGCTCGC GGCCGCCCGG 60

GCCGTAC 67

( 2 ) INFORMATION FOR SEQ ID NO:14:

( i ) SEQUENCE CHARACTERISTICS:
        ( A ) LENGTH: 3323 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

ATAGCCTCCT ATAGGTACCA GACAGGCCGC GGGCACCAGA GTGCCGAGCC CAGGACGCCC 60

```
CCGGCCCAGG  CCCTTGGGGT  GGACAAGTCC  TTCACTTCTC  GCCGGAGTGT  GTGGAGGAGC    120

GATGGGCAGA  ACCAGCACTT  CCCTCAGGCA  CTAGACCTGT  CACGAGTGAA  CTTAGTTCCC    180

TCCTATACTC  CTTCACTCTA  CCCTAAGAAC  ACAGATCTAT  TTGAGATGAT  TGAGAAGATG    240

CAGGGAAGCA  GGATGGATGA  ACAACGCTGC  TCCTTCCCGC  CGCCCCTCAA  AACAGAGGAG    300

GACTACATTC  CATACCCGAG  CGTGCACGAG  GTCTTGGGGC  GAGAAGGACC  CTTCCCCCTC    360

ATCCTGCTGC  CCCAGTTTGG  GGGCTACTGG  ATTGAGGGCA  CCAACCACGA  AATCACCAGC    420

ATCCCCGAGA  CAGAGCCACT  GCAGTCGCCC  ACAACCAAGG  TGAAGCTCGA  GTGCAACCCC    480

ACAGCCCGCA  TCTACCGGAA  GCACTTTCTC  GGCAAGGAGC  ATTTCAATTA  CTACTCACTG    540

GACACTGCCC  TCGGCCACCT  TGTCTTCTCA  CTCAAGTACG  ATGTCATCGG  GGACCAAGAG    600

CACCTGCGGC  TGCTGCTCAG  GACCAAGTGC  CGGACATACC  ATGATGTCAT  CCCCATCTCC    660

TGCCTCACCG  AGTTCCCTAA  TGTTGTCCAG  ATGGCAAAGT  TGGTGTGTGA  AGACGTCAAT    720

GTGGATCGGT  TCTATCCTGT  GCTCTACCCC  AAGGCTTCCC  GGCTCATCGT  CACCTTTGAC    780

GAGCATGTCA  TCAGCAATAA  CTTCAAGTTT  GGCGTCATTT  ATCAGAAGCT  TGGGCAGACC    840

TCCGAGGAAG  AACTCTTCAG  CACCAATGAG  GAAAGTCCCG  CTTTCGTGGA  GTTCCTTGAA    900

TTTCTTGGCC  AGAAGGTCAA  ACTGCAGGAC  TTTAAGGGGT  TCCGAGGAGG  CCTGGACGTG    960

ACCCACGGGC  AGACGGGGAC  CGAATCTGTG  TACTGCAACT  TCCGCAACAA  GGAGATCATG   1020

TTTCACGTGT  CCACCAAGCT  GCCATACACG  GAAGGGACG   CCCAGCAGTT  GCAGCGGAAG   1080

CGGCACATCG  GGAACGACAT  CGTGGCTGTG  GTCTTCCAGG  ATGAAAACAC  TCCTTTCGTG   1140

CCCGACATGA  TCGCGTCCAA  CTTCCTGCAT  GCCTACGTCG  TGGTGCAGGC  TGAGGGCGGG   1200

GGCCCTGATG  GCCCCCTCTA  CAAGGTCTCT  GTCACTGCAA  GAGATGATGT  GCCCTTCTTT   1260

GGACCCCCCC  TCCCGGACCC  CGCTGTGTTC  AGGAAGGGGC  CTGAGTTCCA  GGAATTTTTG   1320

CTGACAAAGC  TGATCAATGC  TGAATATGCC  TGCTACAAGG  CAGAGAAGTT  TGCCAAACTG   1380

GAGGAGCGGA  CGCGGGCCGC  CCTCCTGGAG  ACGCTCTATG  AGGAACTACA  CATCCACAGC   1440

CAGTCCATGA  TGGGCTTGGG  CGGCGACGAG  GACAAGATGG  AGAATGGCAG  TGGGGCGGC    1500

GGCTTCTTTG  AGTCTTTCAA  GCGGGTCATC  CGGAGCCGCA  GCCAGTCCAT  GGATGCCATG   1560

GGGCTGAGCA  ACAAGAAGCC  CAACACCGTG  TCCACCAGCC  ACAGCGGGAG  CTTCGCGCCC   1620

AACAACCCCG  ACCTGGCCAA  GGCGGCTGGA  ATATCACTGA  TTGTCCCTGG  GAAGAGCCCC   1680

ACGAGGAAGA  AGTCGGGCCC  GTTCGGCTCC  CGCCGCAGCA  GCGCCATTGG  CATCGAGAAC   1740

ATACAGGAGG  TGCAGGAGAA  GAGGGAGAGC  CCTCCGGCTG  GTCAGAAGAC  CCCAGACAGC   1800

GGGCACGTCT  CACAGGAGCC  CAAGTCGGAG  AACTCATCCA  CTCAGAGCTC  CCCAGAGATG   1860

CCCACGACCA  AGAACAGAGC  GGAGACCGCA  GCGCAGAGAG  CAGAGGCGCT  CAAGGACTTC   1920

TCCCGCTCCT  CGTCCAGTGC  CAGCAGCTTC  GCCAGCGTGG  TGGAGGAGAC  GGAGGGTGTG   1980

GACGGAGAGG  ACACAGGCCT  GGAGAGCGTG  TCATCCTCAG  GAACACCCCA  CAAGCGGGAC   2040

TCCTTCATCT  ATAGCACGTG  GCTGGAGGAC  AGTGTCAGCA  CCACTAGTGG  GGGCAGCTCC   2100

CCAGGCCCCT  CTCGATCACC  CCACCCAGAC  GCCGGCAAGT  TGGGGGACCC  TGCGTGTCCC   2160

GAGATCAAGA  TCCAGCTGGA  AGCATCTGAG  CAGCACATGC  CCCAGCTGGG  CTGTTAGCCG   2220

GGCCACCCCC  TCTGAAGGTG  AAACTGAGCA  GATGAGGCCA  CAGAAGCACA  AGGGGAAGGT   2280

GCCGTGTCAA  GCCCAGGCAG  ACGAGACCTC  TGCCCTGAAG  ACCAACACCA  GCCCGTGGGC   2340

TGCCCCCTGC  CTCCCCACCC  TCCCCATGGC  CCACCCATCT  GGGCTGTCTC  TGCAGGGCAG   2400

AGCCGTCCAG  ACCTGGGATC  AGGGAAGCTG  CTGGCATCGT  CCCCACCCCC  AGCCTGGGGG   2460
```

-continued

| | | | | | | |
|---|---|---|---|---|---|---|
| TCTGCGCTGG | GGCAGGGATT | GCTCAGTGGA | AGCAGGACTG | GGGGTCTGGC | TTGCCCCCTC | 2520 |
| CCTGGGCCTC | CATCACCCCT | GAGCATCCCT | CTGGACTCAG | AGGGAACAAG | GTGGGAGAGA | 2580 |
| GAGTTTGAGA | CAGCTCCGTG | TGGAGAGCTT | AGCCCCTGGA | GGCAGCACAA | GGAGGATGTG | 2640 |
| ATATGTGGGG | GAGTGAGCAC | TGGGTTGGGA | GCCGGGTCCT | GGTTTCCAAT | TTGGGTTCTG | 2700 |
| CTGTGTGACT | CTGGGCAAGT | CACTCTCCCT | CTCTGGGCAT | GTCTGCTACA | AATGGACAAG | 2760 |
| ATTATTTCAG | AGGTCACTGA | AGACTGTGAT | TACATGCACC | TGCCTTAGAA | GGTAGGATTT | 2820 |
| TCTTCCCAGG | GACCTCCTAT | CACCCTACCC | TGCTTCTTGA | GGTCCCTGGA | GCCCCAGGTG | 2880 |
| GGCTGAGGGG | CAGGGAGCCG | GCTGTGCCCA | GTATGCCTCC | TGGACCCTCC | AGTTCTGCCA | 2940 |
| CAGGTCTGCC | GATGCCCTGT | CCACTGCCTA | CACATGACAG | ACAAGTAACC | CCCTCATGGG | 3000 |
| GGATGGGGAC | CTACCTGGCT | CCTCAGCCAG | CACCCAGCTT | AACCCCTGCC | ATCCCATGCT | 3060 |
| GGGCCCTCCA | GGCCAAGAGT | CTCAGCTGGC | CGAGAGTCCA | GGCCTTGCCT | CCCCCGACCG | 3120 |
| CCATGGAGGG | GGCAGCCCGG | CACAGCTGCT | GGGAGCCCTT | GTGTGTCTGG | TCACACTTTT | 3180 |
| TAGGCGTCAC | GCCAAAGGCC | AGCCTCCTGG | CCCCAATACC | CATTTTGGAA | GCCCCTGTGG | 3240 |
| CCGTGTGGAT | GTCGGTAACA | GTTGTATAAA | ATAAATTCTA | TTTATCGCTA | TTGTAAAAAA | 3300 |
| AAAAAAAAAA | AAAAAAAAAA | AAA | | | | 3323 |

NATIVE TYPE II GAP, METHODS FOR PURIFYING VARIOUS GAPS AND USES OF GAPS TO DIAGNOSE CANCER

FIELD OF THE INVENTION

The present invention relates to the fields of molecular biology/biochemistry and cancer diagnostics. This application is a continuation-in-part of U.S. patent application, Ser. No. 260,807, filed Oct. 21, 1988, now abandoned, which is the continuation-in-part of U.S. patent application of the same title, "GAP Gene Sequences and Diagnostic Uses Thereof," Ser. No. 230,761, filed Aug. 10, 1988, and abandoned on Feb. 2, 1990, in favor of U.S. patent application Ser. No. 260,807, now abandoned.

BACKGROUND OF THE INVENTION

Several genes have been identified that are thought to play a role in regulating normal cell growth. A subset of these genes, termed ras, consists of at least three members, N-ras H-ras, and K-ras2. Altered forms of ras, termed oncogenes, have been implicated as causative agents in cancer. Both the normal cellular genes and the oncogenes encode chemically related proteins, generically referred to as p21.

Ras oncogenes, and their normal cellular counterparts, have been cloned and sequenced from a variety of species. Comparison of the structures of these oncogenes to their normal cellular counterparts have revealed that they differ by point mutations that alter the amino acid sequence of the p21 protein. Naturally occurring mutations in the ras oncogenes have been identified in codons 12, 13, 59, and 61. In vitro mutagenesis work has shown that mutations in codon 63, 116, 117 and 119 also result in transforming activity. The most frequently observed mutation which converts a normal cellular ras gene into its oncogenic counterpart is a substitution of glycine at position 12 by any other amino acid residue, with the exception of proline. Transforming activity is also observed if glycine is deleted, or if amino acids are inserted between alanine at position 11 and glycine at position 12.

Mutations at position 61 also play an important role in the generation of ras oncogenes. Substitution of glutamine for any other amino acid, except proline or glutamic acid in the cellular ras gene yields ras oncogenes with transforming activity.

In relation to normal cellular ras genes and their oncogenic counterparts, there are at least four known retroviral ras oncogenes which exhibit transforming activity. Unlike their non-retroviral analogues, the retroviral genes exhibit two mutations. The biological significance of these double mutations is at present unclear.

Both the normal ras and oncogenic p21 proteins, regardless of their phylogenetic origin, bind guanine nucleotides, GTP and GDP, and possess intrinsic GTPase activity. See Temeles et al., 1985 *Nature,* 313:700. The significance of these biochemical properties to the biological activities of the ras proteins has been demonstrated as follows: first, microinjection of anti-ras antibodies that interfere with guanine nucleotide binding reverses the malignant phenotype of NIH 3T3 cells transformed by ras oncogenes. See Clark et al., 1985, *PNAS (USA),* 82:5280 and Feramisco et al., 1985, *Nature,* 314:639. Second, ras oncogenic proteins that exhibit mutations which result in the inability of p21 to bind guanine nucleotides do not transform NIH 3T3 cells. Willumsen et al., 1986, *Mol. Cell. Biol.,* 6:2646. Third, some ras oncogenes produce p21 proteins that have much reduced GTPase activity compared to their normal cellular counterparts. The biological role of GTPase activity associated with either ras or its oncogenic counterpart remains unknown.

Recently a cytoplasmic factor has been identified which stimulates normal ras p21 GTPase activity, but does not effect GTPase activity associated with the oncogenic mutants. See M. Trahey and F. McCormick, 1987, *Science,* 238:542. The activity has been associated with a protein, termed GAP, which is the acronym for GTPase activating protein. GAP is thought to be a cytoplasmic protein but is presumably capable of moving from the cytosol to the plasma membrane where it interacts with p21.

As alluded to above, ras oncogenes have been implicated in the development of a variety of tumors, and have been shown to be involved in about 10–40% of the most common forms of human cancer. See H. Varmus, 1984, *Annual Rev. Genetics,* 18:553 and M. Barbacid, 1986, in *Important Advances in Oncology,* ed. B. DeVita, S. Helman, S. Rosenberg, pages 3–22, Philadelphia:Lippincott. For example, ras oncogenes have been consistently identified in carcinomas of the bladder, colon, kidney, liver, lung, ovary, pancreas and stomach. They also have been identified in hematopoietic tumors of lymphoid and myeloid lineage, as well as in tumors of mesenchymal origin. Furthermore, melanomas, teratocarcinomas, neuroblastomas, and gliomas have also been shown to possess ras oncogenes.

Considering the possible association of ras oncogenes and cancer, there has been considerable work focused on diagnostic tests for detecting the presence of the oncogene product, p21, or the mutant oncogenes. Early tests, which are still employed in many instances, identify the presence of ras oncogenes in transfection assays which identify p21 by its ability to transform NIH 3T3 cells. See Lane et al., 1981, *PNAS (USA),* 78:5185 and B. Shilo, and R. A. Weinberg, 1981, *Nature,* 289:607. This method is insensitive, laborious, and to be performed adequately, requires a skilled laboratory technician.

A second diagnostic method centers around oligonucleotide probes to identify single, point mutations in genomic DNA. This technique is based on the observation that hybrids between oligonucleotides form a perfect match with genomic sequences, that is, non-mutated genomic sequences are more stable than those that contain a single mismatch. An example of the latter is a point mutation in p21 associated with the ras oncogenes. Although this technique is clearly more sensitive and easier to perform than the transfection assay, it is nevertheless also cumbersome to perform. This is because there are theoretically almost 100 base substitutions which can yield ras oncogenes. Thus, in order to be able to detect these substitutions, multiple oligonucleotide probes must be employed containing each of the three possible substitutions at a particular residue. See Bos et al., 1985, *Nature,* 315:726 and Valenzuela et al., 1986, *Nuc. Acid Res.,* 14:843.

In addition to the transfection and oligonucleotide assays, additional nucleic acid hybridization techniques have been developed to identify ras oncogenes. One such method is based on the unusual electrophoretic migration of DNA heteroduplexes containing single based mismatches in denaturing gradient gels. See Myers et al., 1985, *Nature,* 313:495. This technique only detects between about 25–40% of all possible base substitutions, and requires a skilled technician to prepare the denaturing gradient gels. More sensitive techniques which are refinements of this technique are described by Winter et al., 1985, *PNAS (USA),* 82:7575 and Myers et al., 1985, *Science,* 230:1242.

Immunologic approaches have been taken to detect the product of the ras oncogenes. Polyclonal or monoclonal antibodies have been generated against the intact ras oncogene p21, or against chemically synthesized peptides having sequences similar to oncogene p21, or the non-transforming counterpart. See U.S. patent application Ser. No. 938,581; EP Patent Publication 108,564 to Cline et al.; Tamura et al., 1983, *Cell,* 34:587; PCT Application WO/84/01389 to Weinberg et al. For the most part antibodies have been disappointing as diagnostic tools with which to identify ras oncogenic p21 in human tissue sections. This is because either the antibodies that have been generated to date recognize the normal cellular ras protein as well as the oncogenic protein, or, in those instances in which a monoclonal antibody has been generated that specifically recognizes the oncogenic protein, non-specific staining of tumor biopsies is still observed.

While ras oncogenic p21 is an effective tumorigenic agent, recent studies have shown that normal ras p21 can induce the malignant phenotype. See Chang et al., 1982, *Nature,* 297:7479 and Pulciani et al., 1985, *Mol. Cell. Biol.,* 5:2836. For example, transfection of normal H-ras DNA has been shown to induce malignant transformation. It is further noteworthy that normal ras gene amplification has been observed in several human tumors, and has an apparent incidence of about 1% (Pulciani, et al., above; Yokota et al., 1986, *Science,* 231:261). The various diagnostic tests used to detect ras oncogenes or oncogenic p21 have been applied to the detection of normal ras p21 with similar limited success.

It should be apparent from the foregoing that while there are a number of diagnostic methods for determining the presence of ras oncogenes, or their transforming proteins, there is still a need for fast and reliable diagnostic methods that will permit the routine identification of a wide variety of ras-related tumors.

The cDNAs coding for bovine (Vogel et al., 1988, *Nature,* 335:90) and for full-length human GAP (Trahey et al., 1988, *Science,* 242:1697) have been isolated using oligonucleotide probes designed from selected peptide sequences of the corresponding GAP proteins. The bovine and the Type I human GAP cDNAs are 96% homologous at the amino acid level. A second cDNA encoding the shorter form of human GAP (hereinafter referred to as Type II GAP) has also been isolated from the human placental cDNA library (Trahey et al., 1988, supra). This GAP cDNA apparently was derived from a second mRNA species, generated by an alternative splicing event. Although detection of native Type II GAP has not been reported, analysis of various human tissues by Northern blotting has identified the mRNA for this GAP form primarily in the placenta (Trahey et al., 1988, supra).

SUMMARY OF THE INVENTION

One aspect of the invention presents methods for purifying recombinant and native GAP (hereinafter also referred to as rGAP and nGAP respectively).

Another aspect of the invention presents substantially pure native Type II GAP, and its N-terminal amino acid sequence.

Another aspect of the invention presents GAP nucleotide sequences, protein and fragments thereof with GAP activity, and anti-GAP antibodies as diagnostics for cancers arising from the expression of oncogenic ras genes.

A further aspect of the invention presents the pLP59-3 recombinant transfer vector containing a sequence encoding the GAP protein, and baculovirus AcGAP 11 containing the pLP59-3 vector.

Further aspects of the invention will become apparent upon consideration of the following description of the invention.

BRIEF DESCRIPTION OF THE DRAWINGS

FIG. 3 shows the Type I GAP amino acid sequence used to generate DNA probes that were used to identify the λgt11 clone, GAP 6. Also shown is the corresponding DNA encoding sequence with possible codon redundancies.

FIG. 4 shows the DNA probes used to identify GAP 6.

Figure 5A:
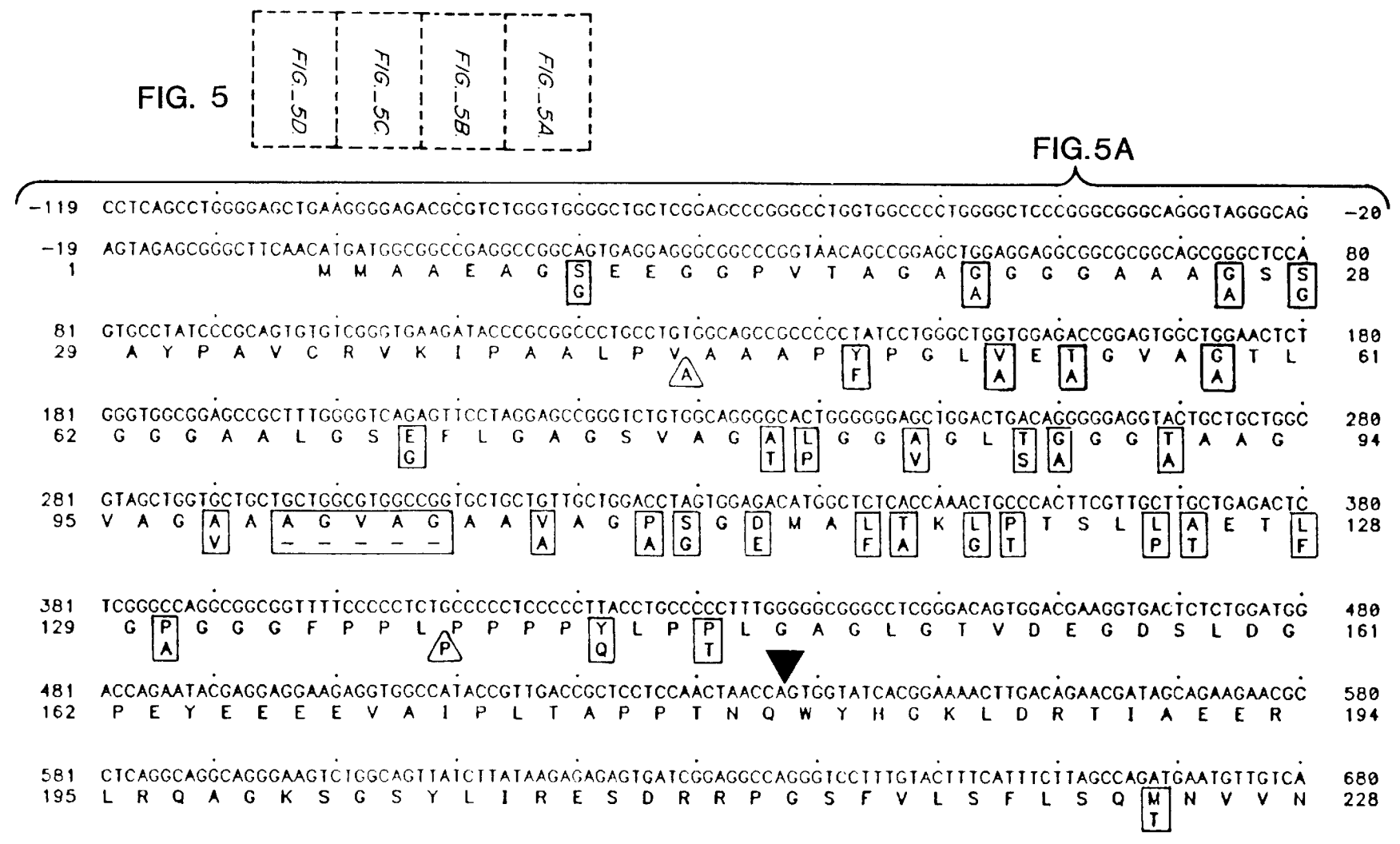

FIGS. 5A through 5D presents the DNA and amino sequence of λ clone, clone 101.

FIGS. 10A and 10B show cation exchange chromatography of crude nGAP preparation. Placental homogenate was fractionated by ammonium sulfate precipitation and chromatographed on an S-Sepharose column.

FIG. 10A shows absorbance at 280 nm and GAP activity assayed by immunoprecipitation and thin layer chromatography (TLC).

FIG. 10B shows an autoradiogram of the Western blot analysis of the S-Sepharose column fractions probed with anti-GAP antibody and $^{125}$I-protein A. The two major GAP bands are indicated by arrows. Fractions 72–82 were pooled as GAP peak I, and fractions 108–120 as GAP peak II.

FIG. 11 shows SDS-PAGE analysis of native GAP purification. Samples were electrophoresed on a 8% SDS-polyacrylamide gel and stained with Coomassie blue. Lane 1, placental homogenate; lane 2, resuspended 50% ammonium sulfate pellet; lane 3, S-Sepharose pool I; lane 4, DEAE-high performance liquid chromatography (HPLC) pool I; lane 5, sulphopropyl high performance liquid chromatography (SP-HPLC) pool I; lane 6, Sepharose pool II; lane 7, DEAE-HPLC pool II.

FIG. 12 shows the N-terminal sequence predicted for Type I nGAP. No N-terminal sequence was detected for Type I nGAP by Edman degradation presumably due to blockage at the N-terminus. The first 20N-terminal amino acids of Type II nGAP were obtained by direct sequencing (out to residue 197, using Type I GAP amino acid numbering).

FIGS. 13A and 13B show the separation of Types I and II nGAP by molecular sieve chromatography. A clarified placental homogenate was fractionated by molecular sieve chromatography on a Sepharose 12 column.

FIG. 13A displays absorbance at 280 nm and GAP activity assayed by immunoprecipitation and TLC, shows the conversion of ras-bound GTP to GDP.

FIG 13B shows an autoradiogram of a Western blot of the column fractions probed with anti-rGAP antibody and $^{125}$I- protein A. Molecular weight (hereinafter referred to as MW) standards were: thyroglobulin (void volume), bovine gamma globulin (160 kD), chicken ovalbumin (43 kD), bovine myoglobin (17 kD), and cyanocobalamin (1.3 kD).

Figure 14:
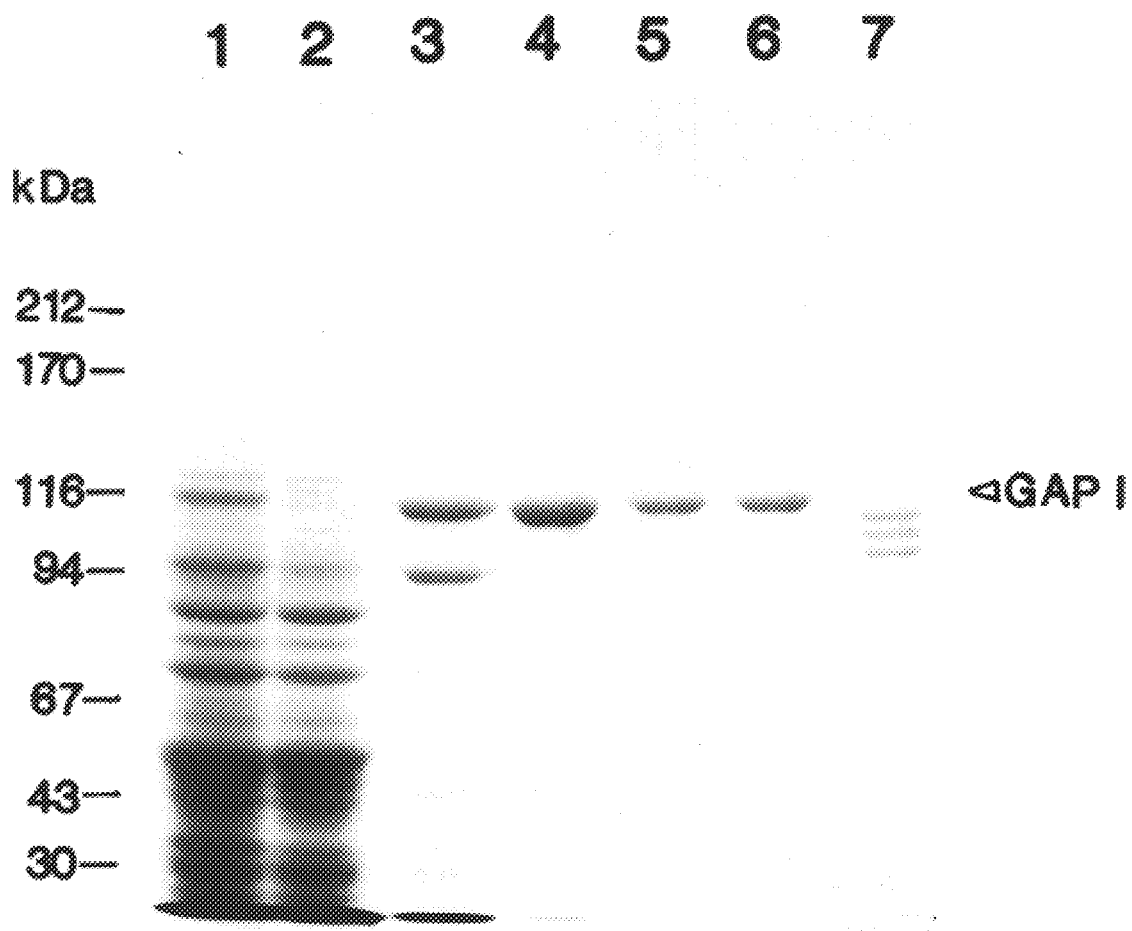

FIG. 14 shows the SDS-PAGE analysis of rGAP purification. Samples were electrophoresed on a 6% SDS-polyacrylamide gel and stained with Coomassie blue. Lane 1, insect cell homogenate; lane 2, S-Sepharose column unbound fraction; lane 3, S-Sepharose column pool; lane 4, S-200 column pool; lane 5, DEAE-HPLC pool 1; lane 6, DEAE-HPLC pool 2; lane 7, partially-proteolyzed preparation of purified Type I rGAP.

FIG. 15 shows the Western blot analysis using anti-rGAP antibody. Samples were electrophoresed on an 8% SDS-polyacrylamide gel, transferred to nitrocellulose by electroblotting, and probed with the anti-rGAP antibody detected by $^{125}$I-protein A. Lane 1, 50 ng of rGAP; lane 2, 10 ng; lane 3, 2 ng; lane 4, 0.4 ng; lane 5, purified native Type I GAP; lane 6, DEAE-purified Type II nGAP. Lanes 7–11 contain 20 μg of protein from a clarified, homogenate of: placenta, lane 7; fetal brain, lane 8; fetal lung, lane 9; fetal liver, lane 10; human breast carcinoma cell line SKBR-3, lane 11. The autoradiogram is a 4-hour exposure with a Lightening Plus screen at −70° C.

DETAILED DESCRIPTION OF THE INVENTION

A better understanding of the invention described herein will be realized by providing a brief description of some of the materials and methods used in the invention.

The normal cellular ras gene and its oncogenic counterparts are defined as described by N. Barbacid, 1987, *Ann. Rev. Biochem.* 56:779. Similarly, the proteins encoded by these genes are also defined as described by Barbacid. Moreover, it will be appreciated that fragments of normal cellular ras p21 that bind GTP, and exhibit GAP stimulated GTPase activity are intended to come within the definition of ras p21.

GAP is an acronym for guanine triphosphatase (GTPase) activating protein and includes both native and recombinant Type I and Type II GAPs. Type I and Type II GAP are defined as proteins having molecular weights and amino acid sequences as described herein. In one aspect, GAP has the further properties of stimulating GTPase activity of normal cellular ras p21, while having little or no stimulatory activity when combined with oncogenic ras p21 proteins and GTP. However, GAP also possesses other activities, apart from the above GTPase stimulatory activity. For example, the non-catalytic domains of GAP (that is, the domains of GAP which do not stimulate the GTPase activity of ras p21) include the SrC homology 2 (SH2) domains which bind to activated platelet derived growth factor receptor (PDGF-receptor) and thereby couple growth factor stimulation to intracellular signal transduction pathways (Pawson et al., 1990, *Sci.*, 250: 979). Therefore, the definition of GAP also include its non-catalytic domains that exhibit activities. In addition, GAP or fragments thereof which exhibit activities are included in the definition of GAP. Such activities include immunogenic activities. For example, fragments exhibiting immunogenic activities would be useful for the production of antibodies against GAP. Of course, it will be understood by those skilled in the art that GAP may also exist as aggregates or multimers under certain conditions, and these forms are intended to come within the scope of the definition. Moreover, the definition is further intended to cover fragments of GAP that exhibit activity.

It will further be appreciated with regard to the chemical structure of GAP, that its precise structure may depend on a number of factors. As all proteins contain ionizable amino and carboxyl groups, it is, of course, apparent that GAP may be obtained in acid or basic salt form, or in neutral form. It is further apparent, that the primary amino acid sequence may be augmented by derivatization using sugar molecules (glycosylation) or by other chemical derivatizations involving covalent or ionic attachment to GAP with, for example, lipids, phosphate, acetyl groups and the like, often occurring through association with saccharides. These modifications may occur in vitro or in vivo, the latter being performed by a host cell through post-translational processing systems. It will be understood that such modifications, regardless of how they occur, are intended to come within the definition of GAP so long as the activity of the protein, as defined herein, is not significantly altered.

As used herein, "chromatography" is defined to include application of a solution containing a mixture of compounds to an adsorbent, or other support material which is eluted, usually with a gradient or other sequential eluant. Material eluted from the support matrix is designated eluate. The sequential elution is most routinely performed by isolating the support matrix in a column and passing the eluting solution(s), which changes affinity for the support matrix, either stepwise or preferably by a gradient, through the matrix. It will be appreciated that encompassed within the definition "chromatography" is the positioning of the support matrix in a filter and the sequential administering of eluant through the filter, or in a batch-mode.

The phrase "hydrophobic interaction matrix" is defined to mean an adsorbent that is a hydrophobic solid such as polystyrene resin beads, rubber, silica-coated silica gel, or crosslinked agarose sufficiently substituted with hydrophobic functional groups to render the material hydrophobic. Alkyl substituted agarose and aryl substituted agarose such as, for example, phenyl or octyl agarose are representative hydrophobic materials. Mixtures of materials that are chromatographically separated on a hydrophobic interaction chromatography matrix are generally first adsorbed to the matrix in a high salt solution, and subsequently desorbed from the matrix by elution in a low salt solution, or a hydrophobic solvent such as a polyol.

"Anion exchange matrix" is defined to mean a solid or gel support matrix that is charged in aqueous solutions. The support matrix may be agarose sufficiently substituted with amine functional groups to have a net charge in aqueous solutions. The material to be adsorbed is generally bound to the anion exchange matrix in a low salt solution and is generally eluted from the anion exchange matrix in a high salt eluant containing anions such as chloride ion which bind to the anion exchange matrix and displace the adsorbed material.

By the phrase "high salt concentration conditions" is meant an aqueous solution wherein an ionic substance is present to create conditions of high ionic strength. Ionic strength is defined as is generally understood in the art and can be calculated from the putative concentrations of the various ions placed in solution modified by their activity coefficient. High salt concentrations that are routinely employed are typified by solutions containing high concentrations of ammonium sulfate; however, other salts, such as sodium chloride, potassium chloride, sodium sulfate, sodium nitrate, or sodium phosphate may also be employed.

The definition of "affinity chromatography" is understood to be similar to that of Wilchek et al., 1984, *Methods in*

*Enzymology*, 104:3. In its broadest intended definition, "affinity chromatography" is a "method of purification based on biological recognition". Briefly, the procedure involves coupling a ligand to a solid support, and contacting the ligand with a solution containing therein a ligand recognition molecule which binds to the ligand. Subsequently, the ligand recognition molecule is released from the ligand and isolated in pure form. It will be understood that a variety of ligands can be employed in affinity chromatography as discussed by Wilchek, et al., and examples of these include lectins, antibodies, receptor-binding proteins and amino acids.

"Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment. However, such altered progeny are included when the above terms are used.

General Description

The invention described herein draws on previously published work and pending patent applications. By way of example, such work consists of scientific papers, patents, or pending patent applications. All of these publications and applications, cited previously or below are hereby incorporated by reference.

Although similar or equivalent methods and materials may be employed in the practice or testing of the present invention, the preferred methods and materials are hereby described.

The instant invention provides methods for purifying both native and recombinant GAP, the methods are preferably applied to purify rGAP from insect cells infected with viruses which carry DNA sequences that encode GAP. Also disclosed are substantially pure native Type II GAP and its partial amino acid and nucleotide sequences. Further disclosed are the pLP59-3 recombinant transfer vector containing a sequence encoding the human recombinant Type I GAP protein, and baculovirus AcGAP 11 containing the pLP59-3 vector.

Further disclosed are description of DNA sequences that encode GAP, and materials and methods for identifying and isolating the same. The DNA sequences, or fragments derived therefrom, are useful as cancer diagnostics, being particularly useful to diagnose for ras p21 related cancers. The identification and isolation of the instant GAP DNA sequences is facilitated by the availability of DNA oligonucleotide probes substantially homologous to the GAP sequence. Because such probes were generated based on a knowledge of the partial amino acid sequence of GAP, the order of discussion of the invention will be: purification of GAP; methods of assaying GAP; the partial amino acid sequence of GAP; cloning of GAP using GAP probes based on the amino acid sequence and the identification of GAP DNA sequences in a cDNA library, along with subcloning of the sequences. In this section is also described the expression of the GAP sequences along with methods of using the same to diagnose for cancer.

GAP Purification

Guanosine triphosphatase activating protein, or GAP, is widely expressed in higher eukaryotes. GAP activity has been detected in cell extracts from human and mouse normal tissues including brain, liver, placenta, B cells, and platelets. It has additionally been found in non-transformed cell cultures including NIH 3T3, as well as transformed cell lines, including human mammary cancer cells (MCF-7), retinoblastoma cells (Y79), and Wilm's tumor (G401). Native GAP activity has been observed in insect cells such as, for example, *Spodoptera fragipedra*. From many of these cells or tissues, GAP may be isolated, albeit with variations in the purification protocols and methods described herein. To the best of applicants' knowledge, though a cDNA believed to encode human Type II GAP has been disclosed, native Type II GAP had not been purified nor sequenced before the work described in this patent application.

The two general methods for purifying GAP from native or recombinant sources are presented below as Methods 1 and 2.

Method 1:

The general scheme for Method 1 GAP isolation and purification consists of releasing the molecule from the cytoplasm of appropriate cells, tissues or organs, followed by removing insoluble material and subjecting the soluble GAP fraction to cation exchange chromatography, followed by a second chromatographic step wherein the eluant from the cation exchanger is passed over an anion exchanger. GAP is eluted from the anion exchanger, and further purified by subjecting it to a third chromatographic step, either hydrophobic chromatography, or a second cation exchange step.

The GAP may be extracted from the different sources by various means. More specifically, GAP is prepared by releasing the molecule from the cytosol using any number of techniques including freeze thawing, sonication, mild detergent extraction, mechanical homogenization etc. The alternative method involves gas cavitation which is discussed below in further detail under the heading of "Method 2".

The extraction procedure is preferably carried out in a physiologically buffered solution containing one or more protease inhibitors. Moreover, to further inhibit protease activity, especially those proteases that rely on metal ions for activity, the extraction solution may contain metal ion chelators. The preferred extraction solution is a physiologically balanced salt solution containing the chelators ethylenegly-coltrichloroacetic acid (EGTA), or ethylenediaminetrichloroacetic acid (EDTA), plus the protease inhibitor phenylmethylsulfonyl fluoride (PMSF). The metal ion chelator(s), as well as the protease inhibitor(s) are present at concentrations that effectively inhibit proteolysis, preferably about 5 mM and 100 $\mu$M, respectively. However, it will, of course, be appreciated by those skilled in the art that since the types and amounts of proteases vary depending on the starting material used to extract GAP, the concentrations that the protease inhibitors or chelators are used at, if indeed used at all, will also vary.

The mixture containing GAP is clarified by centrifugation, or in other ways to remove insoluble material from the aqueous cytosol fraction. If the cytosol fraction contains low amounts of GAP it can be concentrated by any one of several techniques well known to those skilled in the art, including high salt precipitation, such as, for example, with ammonium sulfate, or by ultra filtration. If GAP is concentrated by precipitation, it is preferably subsequently resuspended in a suitable physiologically balanced salt solution containing protease inhibitor(s) and preferably about 0.1% of a nonionic detergent, such as NP40. This solution is then prepared for ion exchange chromatography by dialyzing it against a compatibly buffered chromatographic solution, preferably containing millimolar phosphate, a metal ion chelator, a reducing agent, and a protease inhibitor.

Additionally, because GAP activity is stimulated by the presence of divalent cations such as magnesium chloride, it may also be present in the solution. The pH of the solution is preferably about 6.0.

The GAP dialyzate is then subjected to chromatographic purification consisting preferably of three steps. The first involves purification using an ion exchange chromatographic step compatible with the GAP extraction buffer. Since the preferred extraction buffer contains phosphate, the initial step is purification of GAP by cation exchange chromatography. The second consists of ion exchange chromatography wherein the ion exchange matrix has the opposite ion binding capacity from that of the first ion exchanger employed.

Thus, the preferred purification scheme will consist of applying the phosphate solution containing GAP to a cation exchanger, and eluting GAP therefrom, preferably using solutions which alter the pH or conductivity of the solution. More preferably, GAP will be eluted by applying either a gradient or non-gradient salt solution, and most preferably will be eluted using a linear gradient of sodium chloride over the range of about 0–0.6 molar.

The preferred cation exchanger is a SP-cellulose cation exchanger. Such are commercially available from AMF Molecular Separations Division, Meridian, Conn. under the brand name ZetaPrep SP cartridges. The SP-cellulose cation exchanger is an elastic 3-dimensional network composed of cellulosic backbones cross-linked with vinyl polymer containing pendant sulfopropyl functional groups. The matrix is preferably adapted for radial flow passage of the GAP solution. The flow rate of the solution through the matrix will depend upon the size and geometry of the matrix used. It will be apparent to those skilled in the art, however, that care should be taken to avoid exceeding the unit capacity of the matrix with GAP. If the capacity is exceeded, GAP will not be totally retained and excess unretained GAP will be present in the effluent. The capacity of the matrix to retain GAP can be monitored by assaying for GAP in the effluent using one of the assays described below.

Fractions containing GAP are prepared for the second chromatographic step, that is, anion exchange chromatography. This consists of combining the fractions and adjusting the solution to a pH, and ionic strength compatible with anion exchange chromatography. A variety of anion exchangers are available, and depending on the type employed, the concentrations of these reagents will vary. DEAE-Sepharose or TSK-DEAE-5-PW may be employed. The general procedures for preparing and using these matrices are known to those skilled in the art. The preferred anion exchanger is TSK-DEAE-5-PW matrix. It is prepared by equilibrating it with a solution containing chloride ions at a pH of 8.5. More preferably, the solution will consist of Tris hydrochloride, pH 8.5 plus a reducing agent, a metal chelator, magnesium chloride, and a protease inhibitor. The concentrations of the metal chelator and protease inhibitor will vary and depend on how extensively GAP is proteolyzed, and whether the proteases responsible are activated by metal ions. The concentration of divalent cations, such as magnesium chloride and reducing agent can be determined empirically by monitoring GAP activity. Those concentrations which maintain the highest activity will be utilized. Generally, it is preferred that magnesium chloride and the reducing agent be present in the range of about 0.5–1 mM, and 0.1–1 mM, respectively.

The solution is then passed through the anion exchange matrix whereupon GAP binds to the matrix. GAP is subsequently eluted from the matrix using solutions which alter the pH or conductivity. The preferred elution method consists of eluting GAP using a linear salt gradient ranging from 0–0.6 molar sodium chloride. The purity and activity of GAP so obtained can be monitored by the GTPase assay described below, and by sodium dodecyl sulfate polyacrylamide gel electrophoresis run under reducing conditions. Using these techniques it was determined that Type I GAP has a MW of about 115,000–120,000 daltons.

The third chromatographic step consists of applying, after the anion exchange chromatography, either a second cation exchange step, or a hydrophobic interaction chromatographic step. The most preferred purification scheme utilizes a second cation exchange step. Application of either of these methods will generally increase the purity of GAP to about 95%. If a cation exchange column is chosen, the materials and methods described above are similarly applicable here. Generally, this will consist of decreasing the salt concentration present in the anion column eluates and adjusting the pH to about 6.0. Here, as in the initial cation chromatographic step, several different types of cation exchange matrices can be employed; however, the preferred matrix is a SP-TSK column which is run under high pressure. If hydrophobic chromatography is selected, the ionic strength of the eluate from the anion exchanger should be increased to be compatible with hydrophobic interaction chromatography. The solution can then be passed through a hydrophobic interaction chromatographic matrix, and eluted using techniques known in the art, including decreasing the salt concentration, or eluting with a chaotropic agent. Either of the latter solutions may be used alone, or in combination.

A variety of hydrophobic interaction chromatographic matrixes may be utilized. Generally, the materials and methods for utilizing hydrophobic chromatography are described by S. Shaltie, 1984, *Methods in Enzymology*, 104:69. While it is apparent there are many hydrophobic chromatographic materials and methods that may be employed to purify GAP, phenyl Sepharose is preferred, and it is further preferred that the chromatography be employed under high pressure. The general procedures for forming high pressure liquid chromatography involving a phenyl derivatized matrix are described by F. Regmaer, 1983, *Methods in Enzymology*, 91:137. The preferred phenyl derivatized matrix is available commercially from Bio-Rad Corporation, and is sold under the trade name Biogel TSK phenyl-5-PW.

It will be additionally appreciated by those skilled in the art that an alternative purification scheme may consist of a cation and anion chromatographic exchange step, followed by an affinity chromatographic step. This may be achieved by binding GAP to one or more plant lectins having a known carbohydrate specificity compatible with carbohydrates which may be present on GAP, or by binding GAP to anti-GAP antibodies. In either event, GAP can then be released from the affinity matrix using the appropriate sugar if the matrix is composed of a lectin, or by pH or chaotropic agents if the matrix is composed of antibody.

Because GAP is a protease-sensitive molecule that is broken down into lower species having GAP activity, in a preferred embodiment of the invention the entire purification procedure is carried out rapidly in the cold to minimize proteolytic degradation. In general, this temperature is in a range below 10° C., with a preferred temperature range being about 2°–8° C. Most preferred is a temperature of about 4° C.

Finally, it should be noted that while the preferred applications of the ion exchange materials described herein are in a column format, it will be appreciated that they may also be used in batch format as well.

A preferred embodiment purification scheme consists of isolating Type I GAP from human placentas as follows.

Type I GAP was isolated from 300 g of human placenta by the following three-step chromatographic procedure. Placentas were obtained shortly after delivery, and kept on ice until they were processed. After it was determined by standard tests that the placentas were free of HIV antibodies, they were processed as follows. The initial step consisted of mechanically removing connective tissue, and ridding the placentas of excess blood by multiple soakings in phosphate buffered saline (PBS). The placentas were then fragmented by freezing the tissue at −70° C., followed by placing the tissue in solution of PBS containing 5 mM EGTA, 100 μM PMSF and disrupting the tissue in a blender until a uniform, fine suspension was apparent. The suspension was centrifuged at 100,000×g to remove insoluble debris, the supernatant removed and the proteinaceous material therein precipitated with 40% ammonium sulfate. The ammonium sulfate was removed, and the precipitated proteins resuspended in PBS containing 0.1% NP40 and 100 μM PMSF. This solution was immediately dialyzed against 20 mM potassium phosphate, 1 mM MgCl$_2$, 5 mM EGTA, 0.1 mM dithiothreitol (DTT), 100 μM PMSF, pH 6.1 for six hours. This solution was then immediately chromatographed on a cation matrix, S-Sepharose (fast flow, obtainable from Pharmacia Corporation), pre-equilibrated in 20 mM potassium phosphate, 1 mM MgCl$_2$, 5 mM EGTA, 0.1 mM DTT, 100 μM PMSF, pH 6.1.

Figure 1:
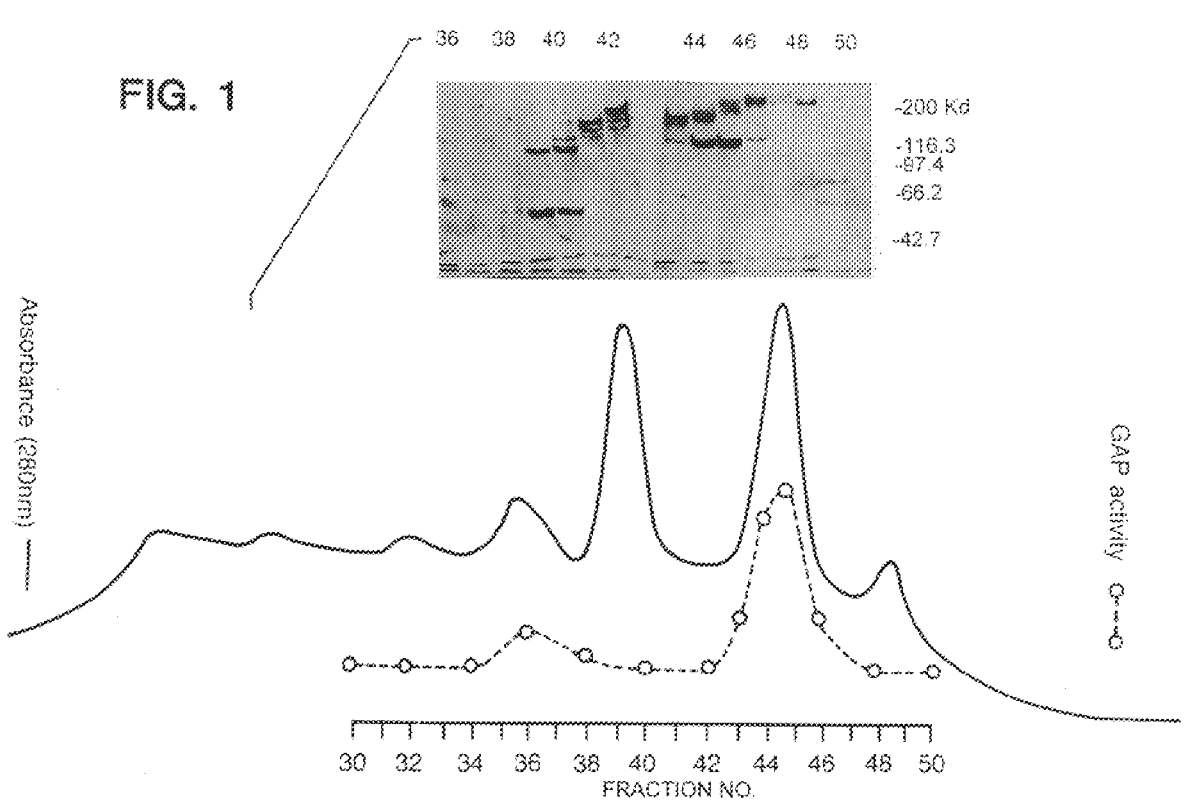
FIG. 1 shows the TSK phenyl column elution profile of Type I nGAP and silver staining of sodium dodecyl sulfate-polyacrylamide gel electrophoresis (SDS-PAGE) fractions thereof.

Proteins absorbed to the cation exchanger were eluted with a linear salt gradient containing 0–0.6M sodium chloride. Using the GAP assay described below, most of the GAP activity was shown to be present in two peaks, a major peak eluting at a sodium chloride concentration of 100–150 mM, and a minor peak eluting at a sodium chloride concentration of 220–300 mM. The major peak was dialyzed against 30 mM Tris-HCl, 1 mM magnesium chloride, 1 mM EGTA, 0.1 mM DTT, 100 μM PMSF, pH 8.5. The dialyzate was applied to an anion exchange column, TSK-DEAE-5-PW (150×21.5 mm). The anion exchange matrix was treated with a linear salt gradient ranging from 0–0.6M sodium chloride to elute the adherent proteins. Most of the GAP activity eluted at a sodium chloride concentration of about 130 mM NaCl. Those fractions containing GAP activity were pooled, brought to 0.5M ammonium sulfate, and passed through a hydrophobic column, phenyl-TSK HPLC. Proteins were eluted from the hydrophobic column using a crisscross gradient consisting of increasing ethylene glycol 0–30%, and decreasing ammonium sulfate, 0.5M–0. The majority of GAP activity eluted at a concentration of 24% ethylene glycol and 0.1 molar ammonium sulfate. GAP activity assays, as performed below, correlated with a protein band of about 120,000 daltons, as revealed by sodium dodecyl sulfate polyacrylamide gel electrophoresis on 6% gels run under reducing conditions (FIG. 1).

A second embodiment purification scheme was employed to purify Type I GAP. Human placentas were again obtained shortly after delivery, soaked in ice cold PBS, homogenized and clarified as described below. Ammonium sulfate was again added to the clarified homogenate to a final concentration of 40% to precipitate proteinaceous material. The ammonium sulfate solution was allowed to stand for one hour at 4° C. prior to recovering the precipitated proteinaceous material by centrifugation for 15 minutes at 10,000×g. The pellet was resuspended in PBS containing 0.1% NP40 and 100 μM PMSF. This solution was dialyzed for six hours at 4° C. against 20 mM potassium phosphate, pH 6.1, containing 1 mM MgCl$_2$, 5 mM EGTA, 0.1 mM DTT, and 100 μM PMSF. Because GAP is susceptible to proteolysis, longer dialysis times are not desirable.

The GAP dialyzate was diluted three-fold with 4 mM potassium phosphate, pH 6.1, containing 0.02M MgCl$_2$, 1 mM EGTA, 0.1 mM DTT, and 100 μM PMSF to lower the ionic strength of the solution. This ionic strength is compatible with application of the dialysate to a S-Sepharose cation exchange column. The dialysate was clarified by centrifugation at 10,000×g for 10 minutes, followed by a further clarification step consisting of filtration through a 0.45 μM filter, prior to adding the dialysate to the S-Sepharose column (fast-flow, Pharmacia). Most of the contaminating proteins passed through the S-Sepharose column, and the adsorbed proteins eluted with a 1.5 liter salt gradient consisting of 0–0.6M NaCl. Those fractions containing GAP activity were identified using the GAP assay described below.

It was again observed that GAP activity eluted from the cation exchange column in predominantly two major peaks. The first peak eluting over a sodium chloride concentration of 100–150 mM was pooled and dialyzed against 30 MM Tris-HCl buffer, pH 8.5 containing 1 mM EGTA, 1 mM MgCl$_2$, 0.1 mM DTT and 100 μM PMSF. The solution was dialyzed at 4° C., and clarified by filtration with a 0.45 μM filter. The filtrate was divided into equal halves, and each half purified using two consecutive anion exchange columns.

Figure 2:
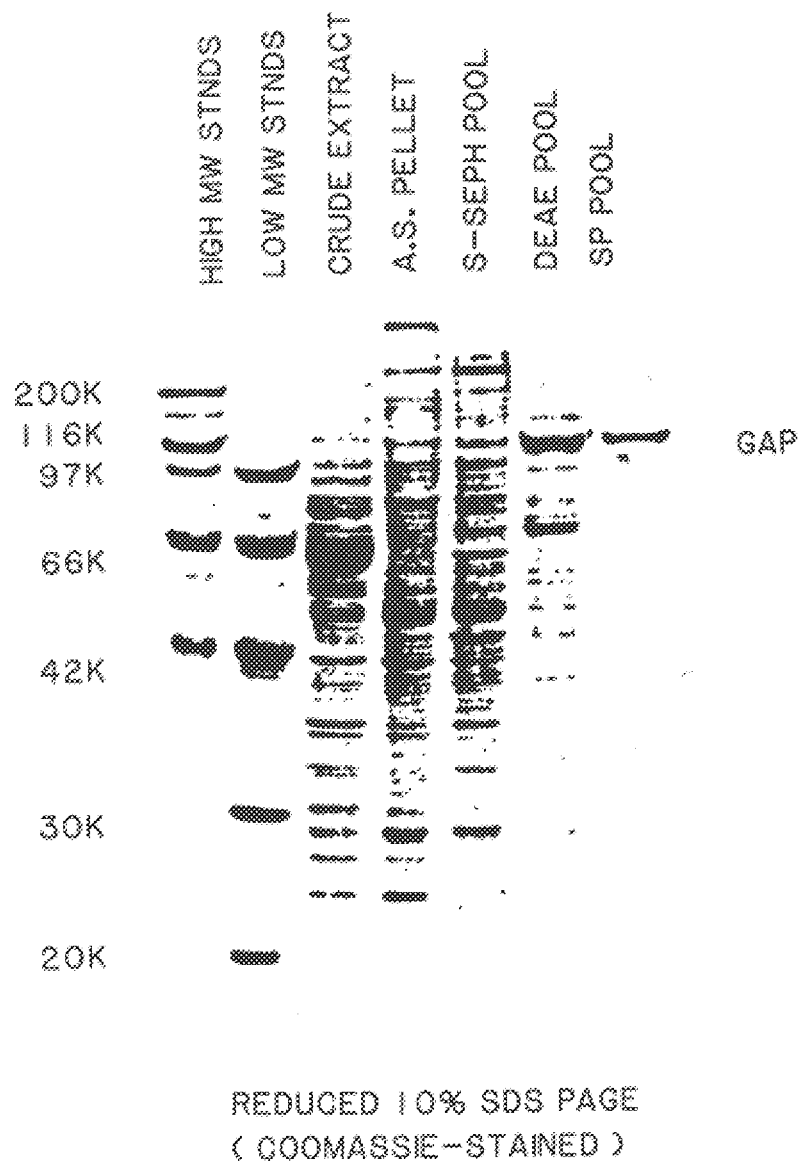
FIG. 2 shows the SDS gel profile of Type I nGAP purified by a three-step chromatographic scheme consisting of cation, and anion chromatography, followed by a second cation chromatographic step.

The two filtrates were separately loaded onto a TSK-DEAE-5-PW column having the dimensions 150×21.5 mm. The column was pre-equilibrated in the Tris-hydrochloride, pH 8.5 dialysis buffer described above. Type I GAP was eluted from the column with a 60-minute 0–0.6M NaCl gradient with a flow rate of 3 ml/minute. The majority of the Type I GAP activity from both filtrates eluted as a single peak at a sodium chloride concentration of about 130 mM. Sodium dodecyl sulfate polyacrylamide gel electrophoretic analysis of the DEAE fractions showed that GAP was the major protein in the peak activity fractions. Fractions containing GAP from both purifications were pooled and diluted 5-fold into 2 mM potassium phosphate, pH 6.1, containing 0.1 mM EGTA, 10 μM DTT, 10 μM PMSF to lower the salt concentration to insure that the solution was chromatographically compatible with a second cation exchange chromatographic step, that is, chromatography with a SP-TSK column. The pH of the solution was checked and adjusted to pH 6.1 with sodium acetate (3M, pH 4.8) if necessary. Both of the GAP fractions isolated from the DEAE columns were further purified separately over a cation column, TSK-SP-5-PW having dimensions of 75×7.5 mm. A solution containing 20 mM potassium phosphate, pH 6.1, containing 1 mM EGTA, 0.1 DTT, and 0.1 mM PMSF was passed through the column, followed by eluting GAP with a 45-minute, 0–0.6M sodium chloride gradient at 1 ml per minute. Those fractions containing GAP were identified using the assay described below and sodium dodecyl sulfate polyacrylamide gel electrophoresis. Type I GAP activity corresponded to a protein having a MW of about 116,000 daltons. Amino acid analysis was performed on the purified GAP to determine protein concentration. Starting with about 300 grams of human placenta, approximately 430 micrograms of purified Type I GAP was obtained. FIG. 2 shows the SDS-PAGE analysis of Type I GAP at the various stages of purification described above.

Method 2:

The following describes an improved method for purifying both native and recombinant GAP. This method has the advantage of producing purified GAP protein with little or no detectable proteolysis by SDS-PAGE analysis. Before applying the Method 2 purification procedure, the nGAP and rGAP can be extracted from their respective sources by means described under Method 1.

The GAP may be purified from various cell sources, for example, the cells can be from placenta expressing native GAP forms, or the preferred example of insect cells carrying recombinant transfer vectors expressing GAP. The procedure involves the use of cation exchange, molecular sizing, and anion exchange chromatography. The preferred purification procedure involves an S-Sepharose purification step that maximizes the separation of GAP from other contaminating proteins. The use of size exclusion chromatography (SEC) and DEAE-HPLC, for example, TSK-DEAE-5-PW (BioRad), further enhances the purity of the GAP obtained.

In addition to the use of protease inhibitors such as leupeptin, the preferred purification procedure has the following safeguards against proteolysis of GAP. Steps were taken to minimize the exposure of rGAP to pHs below 8, at which lysosomal proteases are most active. Molecular sizing chromatography was preferably used in the purification step to separate the proteases from the GAP protein. This step was shown to remove most of the protease activity and substantially reduce degradation as measured by reducing SDS-PAGE of the purified GAP or by Western analysis using anti-rGAP antibody.

The present invention discloses an extraction method which has the advantage of minimizing proteolysis of rGAP and increasing the yield of the pure rGAP. First, instead of freeze thawing, or sonication of the cells, the preferred procedure uses gas cavitation to lyse the cells. The preferred gas is nitrogen. Example 3 below exemplified the nitrogen cavitation method for extracting recombinant GAP from insect cells carrying the GAP expression vector, and further combined it with the purification procedure outlined in Method 2 below, which produced rGAP with minimal or no proteolysis as detected by SDS-PAGE.

As shown in Example 3 below, Method 2 was employed to purify full length rGAP from *Spodoptera frugiperda* (Sf9) cells infected with the baculovirus AcGAP 11 which carried the GAP sequence derived from the transfer vector, pLP59-3. Method 2 had also been employed in the purification and recovery of proteolyzed rGAP fragments of 95 kD in length from the above Sf9 cells. Therefore, this purification method can be used to obtain fragments of GAP. This method can also be used to purify muteins of GAP. It would also be obvious to one skilled in the art that this method would be applicable to other forms of GAP which have similar biochemical properties. For example, this method is applicable to purify native Type II GAP disclosed herein; and rGAP from clones Sleepy and 16.

GAP Assay

Several assays have recently been described to measure GAP activity. M. Trahey and F. McCormick, 1987, *Science*, 238:542; Adari et al., 1988, *Science*, 240:518. These references are herein incorporated in their entirety. GAP may be assayed in vitro, and several different types of in vitro assays can be performed. The preferred assay involves measuring the presence of GDP resulting from the hydrolysis of GTP. This assay involves combining in an appropriate physiologically buffered aqueous solution, empirically determined optimal amounts of normal cellular p21, and α-32P-GTP, plus GAP. The solution may also contain protease inhibitors and a reducing agent.

The reaction solution is incubated for various times and may be conducted at temperatures typically employed to perform enzymatic assays, preferably 10°–40° C., and more preferably at 37° C. At the appropriate times aliquots are removed and assayed for α-32P-GDP. This is readily accomplished by first separating p21 containing bound (α-32P-GDP from the other reactants in the solution, particularly free α-32P-GTP. This can be achieved by immunoprecipitating p21 with antibodies directed thereto. Immune precipitation techniques and anti-p21 antibodies are known, and routinely employed by those skilled in the art. α-32P-GDP, is released from the immune precipitate preferably by dissolving the sample in a denaturing detergent at an elevated temperature, more preferably in 1% sodium dodecyl sulfate at 65° C. for 5 minutes, and chromatographing the mixture on a suitable thin layer chromatographic plate. The chromatography is preferably carried out on a PEI cellulose plate in 1M LiCl. α-32P-GDP is identified by its mobility relative to a known standard using suitable radiodetection techniques, preferably autoradiography.

An alternative assay for GAP activity is to substitute gamma labelled 32P-GTP for α-labelled 32P-GTP in the above assay system, and assay for free 32P labelled phosphate using activated charcoal. This assay can be carried out as described by Tjian et al, 1980, *Cold Spring Harbor Symp. Quant. Biol.*, 44:103.

An additional assay does not involve immune precipitation. Rather, an aliquot from a GAP assay reaction mixture described above can be directly subjected to PEI cellulose chromatography in 1M LiCl. This assay, however, is most useful for assaying solutions having substantially purified GAP.

A typical GAP assay can be carried out as follows. Approximately 0.8 micrograms of H-ras protein obtained as described by Trahey, et al., supra was bound to α-32P-GTP followed by precipitation of the complex with 13 micrograms of an anti-ras antibody, 157–181, that recognizes the carboxyl terminal end of the molecule. Specifically, 157–181 recognizes the carboxyl terminal residues at positions 157–181. Adari et al., 1988, *Science*, 240:518. Next, 10 micrograms of sheep-anti-mouse IgG, and 10 microliters of protein A-Sepharose beads were added. As a control, the same reactants were combined except that rat IgG replaced 157–181, and goat anti-rat IgG replaced sheep anti-mouse IgG. The pellets were washed with 20 mM Tris hydrochloride, pH 7.4, containing 20 mM sodium chloride, 1 mM magnesium chloride and 1 mM DTT and resuspended in the same solution. Four microliter aliquots of the immune complex were then mixed with 10 microliters of GAP, or, as a control, buffer without GAP. After 60 minutes incubation at room temperature the Sepharose beads were washed again, and the bound nucleotides analyzed using thin layer chromatography with 1M LiCl as the solvent. The thin layer plate was autoradiographed for one to two hours after which it was developed. The autoradiograph revealed that addition of sufficient GAP causes the near complete hydrolysis of GTP to GDP, whereas very little GTP hydrolysis occurs in the control lacking GAP. The assay detects GAP in a semi-quantitative, dose-dependent fashion. Quantitation can be improved by scraping the relevant regions of the plate and measuring cpm in GDP by use of a gamma counter. The immune precipitation controls having rat IgG substituted for the mouse antibodies revealed no GTP or GDP.

In addition to the above method, GAP can be preferably assayed as follows. Four $\mu$M normal cellular p21 was dissolved in a buffer containing 80 mM β-glycerophosphate, 5 mM MgCl$_2$, 1 mM DTT, pH 7.5, plus 255 $\mu$M [α-32P] GTP (16 Ci/mmole), 4 mM ATP, and bovine serum albumin (2.5 mg/ml). The mixture was preincubated for 30 minutes at 37° C., followed by the addition of either a sample suspected of containing GAP, or an equal volume of buffer. After one hour at room temperature the monoclonal antibody Y13-259 in the presence of 0.5% NP40 was added in an amount sufficient to bind all the p21 present in the solution. Next, goat anti-Rat Ig-Protein A Sepharose was added to collect p21 bound to Y13-259, and the immune complex isolated and washed ten times in 20 mM Tris-HCl, pH 8.0, 100 mM NaCl, 5 mM $MgCl_2$, and 0.5% NP40. To determine the extent of GTP binding and hydrolysis during these steps a control was run consisting of adding 5 μg of p21 ras immediately before adding Y13-259.

Nucleotides were eluted from p21 with 1% SDS, 20 mM EDTA at 65° C. for 5 minutes and chromatographed on PEI Cellulose in 1M LiCl. GTP and GDP were visualized using standard autoradiographic techniques. The results showed that normal cellular p21 ras affects a nearly complete conversion of GTP to GDP when compared to mutant ras oncogenic proteins Asp 12 and Val 12 assayed similarly. Moreover, little or no GTP or GDP was detected in the control sample.

The assays described above are presented in more detail by Trahey and McCormick, 1987, in Science, 238:542, and by Adari et al., 1988, in Science, 240:518. Both of these references are hereby incorporated by reference.

More specifically, the biological activities of native and recombinant GAP preparations were measured using either an immunoprecipitation assay or a phosphate-release assay. The immunoprecipitation assay (Trahey & McCormick, 1987, Science, supra) was based on the precipitation of N-ras-bound, [$\alpha$-$^{32}$P]guanine nucleotide (70 nM) and measurement of GTP to GDP conversion by autoradiography or scintillation counting of material fractionated by thin layer chromatography (TLC). This assay was used primarily to identify column fractions enriched for GAP activity during protein fractionation procedures. In certain column fractions in which non-specific GTPase activity was absent, the assay was run without an immunoprecipitation step (referred to as a non-IP assay).

The phosphate-release assay, based on release of [$\gamma$-$^{32}$P]-phosphate from N-ras-bound [$\gamma$-$^{32}$P]guanine nucleotide, was performed as a modification of the organic extraction method of Schacter, 1984, Anal. Biochem., 138:416. Samples containing GAP activity were serially diluted in 20 mM Hepes buffer (pH 7.6) containing 1 mM $MgCl_2$, 2 mM DTT, 0.1% NP40, 10 μg/ml leupeptin, 200 μM PMSF, and 1 μg/ml pepstatin. 25 μl of each GAP dilution was equilibrated in a 25° C. water bath. Highly purified GAP preparations (1 mg/ml) were diluted approximately 50,000-fold to measure specific activities.

Prior to initiating the GAP assay, purified recombinant N-ras (Trahey et al, 1987, Mol. Cell. Biol., 7:541) was equilibrated with [$\gamma$-$^{32}$P]GTP for 10 minutes at 15° C. For each reaction, 0.4 μl of [$\gamma$-$^{32}$P]GTP (6,000 Ci/mM) (E. I. Du Pont, NEN® Research Products, Boston, Mass.; hereinafter referred as NEN), 0.1 μl of N-ras (250 μg/ml), and 4.5 μl of 20 mM Tris buffer pH 8.0, containing 1 mM EDTA, 1 mM DTT, 1 mM ATP, and 1 mg/ml BSA was used. The assay was initiated by adding 5 μl of N-ras[$\gamma$-$^{32}$P]GTP to the GAP samples. After 5 minutes at 25° C., 200 μl of 5 mM silicotungstate and 1 mM $H_2SO_4$ was added to stop the reaction. 300 μl of isobutanol/toluene (1:1) was then added followed by 40 μl of 5% ammonium molybdate in 2M $H_2SO_4$. The samples were vortexed on high for 10 seconds and then allowed to sit for 5 minutes during phase separation. 150 μl of the organic phase (upper) was removed and quantitated by measuring Cerenkov radiation. The total amount of [$\gamma$-$^{32}$P]GTP-bound N-ras was calculated by measuring the amount of [$^{32}$P]-phosphate released in tubes having a 200-fold excess of purified GAP (250-fold dilution of 1 mg/ml stock). A cpm-to-pmole conversion factor was determined for each assay and used to calculate pmoles of GTP by comparing the manufacturer's specification of [$\gamma$-$^{32}$P]GTP concentration to the actual cpm measured.

This assay was used to measure the biological specific activities of native and recombinant GAP preparations. 1 unit of GAP activity was defined as one pmole of GTP-bound N-ras converted to GDP per minute at 25° C. at a N-ras-GTP concentration of approximately 18 nM.

GAP Amino Acid Sequence

The GAP protein, or fragments derived therefrom can be sequenced using standard techniques known to those skilled in the art. In the event that GAP is isolated having a blocked amino terminal end, internal sequencing can be achieved by fragmenting the molecule such as, for example, with lysyl endopeptidase, and sequencing one or more of the resulting fragments. Although this may not necessarily be the case for GAP isolated from sources other than placenta, in the instant invention it was determined that Type I GAP exhibited a blocked amino terminal end.

The protein having a MW of about 120,000 obtained by the Method 1 purification described above was electro-eluted from a 6% sodium dodecyl sulfate, polyacrylamide gel in 0.05 molar ammonium bicarbonate containing 0.1% sodium dodecyl sulfate. The procedure followed is essentially that described by Hunkapiller et al., 1983, Methods in Enzymology, 91:227. The electro-eluted protein was fragmented for internal sequencing using lysyl endopeptidase (5% w/w, 18 hours at 40° C., WAKO). Peptides were fractionated by reversed-phase high performance liquid chromatography using a Brownlee Aquapore RP-300 cartridge (100×2.1 mm, Applied Biosystems, Inc., Foster City, Calif.). Peptides were eluted with an Acetonitrile gradient from 0–70% in 120 minutes (Buffer A, 0.1% trifuoroacetic acid (TFA) in $H_2O$; Buffer B, 0.085% TFA in 85% acetonitrile). Automated sequence analysis of the peptides was conducted on an Applied Biosystems 470A gas-phase sequencer as reported. A peptide characteristic of Type I GAP has the following amino acid sequence: I M P E E E Y S E F K.

Cloning of GAP

A full length cDNA sequence that encodes GAP was obtained as follows: first, partial cDNA sequences were identified in a cDNA library using as oligonucleotide probes, DNA sequences derived from the partial amino acid composition of Type I GAP, above. One such partial cDNA sequence, referred to as GAP 6, was subcloned and sequenced Knowledge of its DNA sequence led, in turn, to additional probes that were used to screen cDNA libraries for longer cDNA inserts, eventually yielding the full length clone, clone 101. Each of the various procedures will be discussed below.

1. General Cloning Techniques

Construction of suitable vectors containing the desired GAP coding sequence employs standard ligation and restriction techniques which are well understood in the art. Isolated vectors, DNA sequences, or synthesized oligonucleotides are cleaved, tailored, and religated in the form desired.

Site specific DNA cleavage is performed by treating with suitable restriction enzyme(s) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution. In the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered form aqueous fractions by precipitation with ethanol followed by chromatography using a Sephadex G-50 spin column. If desired, size separation of the cleaved fragments may be performed by polyacrylamide gel or agarose gel electrophoresis using standard techniques. A general description of size separations is found in *Methods in Enzymology*, 1980, 65:499–560.

Restriction cleaved fragments may be blunt ended by treating with the large fragment of *E. coli* DNA polymerase I, that is, the Klenow fragment, in the presence of the four deoxynucleotide triphosphates (dNTPs) using incubation times of about 15 to 25 minutes at 20° to 25° C. in 50 mM Tris pH 7.6, 50 mM NaCl, 6 mM MgCl$_2$, 6 mM DTT and 10 mM dNTPs. After treatment with Klenow, the mixture is extracted with phenol/chloroform and ethanol precipitated. Treatment under appropriate conditions with S1 nuclease results in hydrolysis of single-stranded portions.

Ligations are performed in 15–30 μl volumes under the following standard conditions and temperatures: 20 mM Tris-Cl pH 7.5, 10 mM MgCl$_2$, 10 mM DTT, 33 μg/ml BSA, 10 mM-50 mM NaCl, and 1 mM ATP, 0.3–0.6 (Weiss) units T4 DNA ligase at 14° C. for "sticky end" ligation, or for "blunt end" ligations 1 mM ATP was used, and 0.3–0.6 (Weiss) units T4 ligase. Intermolecular "sticky end" ligations are usually performed at 33–100 μg/ml total DNA concentration. In blunt end ligations, the total DNA concentration of the ends is about 1 μM.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per μg of vector at 60° C. for about 1 hour. Nucleic acid fragments are recovered by extracting the preparation with phenol/chloroform, followed by ethanol precipitation. Alternatively, religation can be prevented in vectors which have been double digested by additional restriction enzyme digestion of the unwanted fragments.

In the constructions set forth below, correct ligations are confirmed by first transforming the appropriate *E. coli* strain with the ligation mixture. Successful transformants are selected by resistance to ampicillin, tetracycline or other antibiotics, or using other markers depending on the mode of plasmid construction, as is understood in the art. Miniprep DNA can be prepared from the transformants by the method of D. Ish-Howowicz et al., 1981, *Nucleic Acids Res.*, 9:2989) and analyzed by restriction and/or sequenced by the dideoxy method of F. Sanger et al., 1977, *PNAS (USA)*, 74:5463 as further described by Messing et al., 1981, *Nucleic Acids Res.*, 9:309, or by the method of Maxam et al., 1980, *Methods in Enzymology*, 65:499.

Host strains used in cloning in M13 consists of *E. coli* strains susceptible to phage infection, such as *E. coli* K12 strain DG98 are employed. The DG98 strain has been deposited with ATCC Jul. 13, 1984 and has Accession No. 1965.

Depending on the host cell used, transformation is done using standard techniques appropriate to such cells. The calcium treatment employing chloride, as described by S. N. Cohen, 1972, *PNAS (USA)*, 69:2110, or the RbCl$_2$ method described in Maniatis et al., 1982, *Molecular Cloning: A Laboratory Manual*, Cold Spring Harbor Press, p. 254 was used for procaryotes. Transfection of Sf9 cells was achieved using a modification of the calcium phosphate precipitation technique (Graham, F. L. et al., 1973, *Virology*, 52:456) as adapted for insect cells (J. P. Burand et al., 1980, *Virology*, 101; E. B. Casstens et al., 1980, *Virology*, 101:311). Additional details regarding transfection of Sf9 cells are described by Summers and Smith in "A Manual of Methods for Baculovirus Vectors and Insect Cell Culture Procedures", Texas A & M Press: 1986. The baculovirus transfer vectors employed herein are derived from transfer vectors which have been described by G. E. Smith et al., 1983, above. These vectors were originally constructed by cloning the AcNPV EcoRI-1 fragment containing the polyhedron gene into the EcoRI site of *E. coli* plasmid pUC8 as described by Vieira et al., 1982, *Gene*, 19:259–268. A family of plasmids having single BamHI cloning sites at various locations in the polyhedron gene were created as described by Smith et al., 1983, above. The most used of these, pAc373, has a unique BamHI site 50 base pairs downstream from the polyhedron cap site, that is to say, 8 base pairs before the polyhedron ATG translation initiation codon (Luckow and Summers, 1988, in *Biotechnology*, 6:47).

2. Oligonucleotide Probes

Synthetic oligonucleotides were prepared by the triester method of Matteucci et al., 1981, *J. Am Chem. Soc.*, 103:3185 or using commercially available automated oligonucleotide synthesizers. Kinasing of single strands prior to annealing or for labelling is achieved using an excess, e.g., approximately 10 units of polynucleotide kinase to 0.1 nmole substrate in the presence of 50 mM Tris, pH 7.6, 10 mM MgCl$_2$, 5mM dithiothreitol, 1–2 mM ATP, 1.7 pmoles gamma $^{32}$P-ATP (2.9 mCi/mmole), 0.1 mM spermidine, 0.1 mM EDTA.

Using the partial GAP amino acid sequence described above, and known codon redundancies thereto, several DNA oligonucleotide probes were synthesized and these are shown in FIGS. 3 and 4.

3. Identification and Isolation of GAP Sequences

Several procedures are available for identifying GAP DNA sequences. The preferred procedure is to use the oligonucleotide probes described above to screen cDNA libraries. cDNA libraries can be constructed using techniques known in the art, or can be purchased commercially.

An illustrative procedure for making a cDNA library containing GAP sequences may consist of isolating total cytoplasmic RNA from suitable starting material, and further isolating messenger RNA therefrom The latter can be further fractionated into Poly (A+) messenger RNA, which in turn is fractionated further still into Poly (A+) messenger RNA fractions containing GAP messenger RNA. The appropriate GAP messenger RNA can then be reverse transcribed and cloned into a suitable vector to form the cDNA library.

More specifically, the starting material (i.e., tissue, cells) is washed with phosphate buffered saline, and a non-ionic detergent, such as ethylene oxide, polymer type (NP-40) is added in an amount to lyse the cellular, but not nuclear membranes, generally about 0.3%. Nuclei can then be removed by centrifugation at 1,000×g for 10 minutes. The post-nuclear supernatant is added to an equal volume of TE (10 mM Tris, 1 mM ethylenediaminetetraacetic acid (EDTA), pH 7.5) saturated phenol/chloroform (1:1) containing 0.5% sodium dodecyl sulfate (SDS) and 10 mM EDTA. The supernatant is re-extracted 4 times and phase separated by centrifugation at 2,000×g for 120 minutes. The RNA is precipitated by adjusting the samples to 0.25M NaCl, adding 2 volumes of 100% ethanol and storing at −20° C. The RNA is then pelleted at 5,000×g for 30 minutes, washed with 70% and 100% ethanol, and dried. This represents the total cytoplasmic RNA. Polyadenylated (Poly A+) messenger RNA (mRNA) can be obtained from the total cytoplasmic RNA by chromatography on oligo (dT) cellulose (J. Aviv et al., 1972, *PNAS,* 69:1408–1412). The RNA is dissolved in ETS (10 mM Tris, 1 mM EDTA, 0.5% SDS, pH 7.5) at a concentration of 2 mg/ml. This solution is heated to 65° C. for 5 minutes, then quickly chilled to 4° C. After bringing the RNA solution to room temperature, it is adjusted to 0.4M NaCl and slowly passed through an oligo (dT) cellulose column previously equilibrated with binding buffer (500 mM NaCl, 10 mM Tris, 1 mM EDTA, pH 7.5). The flow-through is passed over the column twice more, and the column washed with 10 volumes of binding buffer. Poly (A+) mRNA is eluted with aliquots of ETS, extracted once with TE-saturated phenol chloroform and precipitated by the addition of NaCl to 0.2M and 2 volumes of 100% ethanol. The RNA is reprecipitated twice, washed once in 70% and then 100% ethanol prior to drying. The poly (A+) mRNA can then be used to construct a cDNA library.

cDNA can be made from the enriched mRNA fraction using oligo (dT) priming of the poly A tails and AMV reverse transcriptase employing the method of H. Okayama et al., 1983, *Mol. Cell Biol.* 3:280.

Other methods of preparing cDNA libraries are, of course, well known in the art. One, now classical, method uses oligo (dT) primer, reverse transcriptase, tailing of the double stranded cDNA with poly (dG) and annealing into a suitable vector, such as pBR322 or a derivative thereof, which has been cleaved at the desired restriction site and tailed with poly (dC). A detailed description of this alternate method is found, for example, in U.S. Ser. No. 564,224, filed Dec. 20, 1983, and assigned to the same assignee, incorporated herein by reference.

As mentioned above, cDNA libraries are commercially available. A particularly useful library is sold by Clontech (Catalog number #L H1008). It is a λgt11 human placenta cDNA library made from total poly (A+) messenger RNA.

4. Identification of GAP DNA Sequences

The oligonucleotide probes described above, GW13, GW15, GW17 and GW19 were used to screen the commercially available Clontech library. The library was plated at about 50,000 plaques per plate using 17 plates. Thus, about 850,000 plaques were screened using the plaque hybridization procedure. While a variety of such procedures are known, a description of the preferred procedure follows. Each 150 mM plate was replicated onto duplicate nitrocellulose filter papers (S & S type BA-85). DNA was fixed to the filter by sequential treatment for 5 minutes with 0.5N NaOH plus 1.0M NaCl; 1.5M NaCl plus 0.5M Tris-HCl pH 8; and 20 mM Tris plus 2 mM EDTA pH 8. Filters were air dried and baked at 80° C. for 2 hours.

The duplicate filters were prehybridized at 55° C. for 2 hours with 10 ml per filter of DNA hybridization buffer, 5×SSC, pH 7.0, 5×Denhardt's solution (polyvinylpyrrolidone, plus Ficoll and bovine serum albumin; 1×0.02% of each), 50 mM sodium phosphate buffer at pH 7.0, 5 mM EDTA, 0.1% SDS, and 100 $\mu$g/ml yeast RNA. The prehybridization buffer was removed and the samples were hybridized with a mixture of kinased probes under conditions which depend on the stringency desired. About $2\times10^6$ cpm/ml total was used. Typical moderately stringent conditions employ a temperature of 42° C. plus 50% formamide for 24–36 hours with 1–5 ml/filter of DNA hybridization buffer containing probe. For higher stringencies high temperatures and shorter times were employed. The preferred hybridization conditions consisted of hybridizing the probes to the filters in 5×SSC (standard saline citrate), Denhardt's solution, 50 mM NaPO$_4$ pH 7.0, 5 mM EDTA, 0.1% SDS, and 100 mg/ml yeast RNA at 55° C. overnight. Next, the filters were washed twice, 30 minutes each wash, at room temperature with 2×SSC, 0.1 % SDS and 50 mM sodium phosphate buffer pH 7, then washed once with 2×SSC and 0.1% SDS at 50° C., and air dried. Finally, the filters were autoradiographed at −70° C. for 36 hours.

The autoradiographic results revealed a single positive plaque. Using the washing and hybridization conditions described above, several λgt11 plaque purified isolates were identified and picked. Viral DNA was obtained from one of these, termed GAP 6, as follows. GAP 6 was plated at high density on a lawn of *E. coli* strain Y 1090 (r⁻). Following lysis of the *E. coli,* phage particles were eluted into S M buffer (0.1M NaCl 8.1 mM MgSO$_4$ 50 mM Tris-HCl pH 7.5 0.01% Gelatin) by covering the *E. coli* with buffer and incubating the plate in the cold for several hours. The lysate containing phage particles was centrifuged at 11,500×g for 20 minutes to remove cellular debris, and the resulting supernatant titered using standard techniques. A titer of $2\times10^{10}$ PFU/ml was determined. Finally, phage DNA was isolated by the procedure of Maniatis et al., above.

5. Characterization of GAP 6

GAP 6 was subcloned into a suitable vector in order to characterize the DNA both as to EcoRI restriction sites, and partial DNA sequence. Although GAP 6 DNA can be cloned into a variety of vectors, in the instant invention it was cloned into M13. More specifically GAP DNA was cloned into a M13 vector as follows. GAP 6 DNA was treated with EcoRI enzyme which produced two fragments, about 2.0 kb and 0.24 kb. These fragments were isolated using standard agarose gel techniques, and ligated into M13mp18. The M13 vector was designed so that vectors without DNA inserts show up blue under the proper culture conditions, whereas vectors with a DNA insert are clear.

The ligated M13mp18 phage were transduced into frozen competent *E. coli* K12 strain DG98 and cultured by plating on media containing 5×10-4M isopropyl thiogalactoside (IPTG) obtained from Sigma Chem. (St. Louis, Mo.) and 40 $\mu$g/ml X-gal. Non alpha-complementing white plaques were picked onto fresh media. Mini-cultures were screened for recombinant single strand phage DNA containing inserts.

The white M13 plaques were screened for inserts by direct gel electrophoresis. The latter procedure was conducted essentially as described by J. Messing, 1983, *Methods of Enzymology,* 101:20, which is hereby incorporated by reference. Four M13mp18 subclones were identified by this method. Two subclones, GAP 2 and GAP 8, contained the 2 kb fragment in both orientations. The remaining two subclones, GAP 12 and GAP 18, contained the 0.24 kb fragment in both orientations.

The partial DNA sequence of GAP 2 and GAP 8 was determined by the method disclosed in T. Sanger, S. Nicklen, and H. R. Coulson, 1977, *PNAS (USA),* 74:5463–5467 techniques described above:

5' AAAACTCATGC AAGGGAAGGG CAAAACCCAG TATGGTCAGA

AGAGTTTGTC TTTGATGATC TTCCTCCTGA CATCAATAGA

-continued

TTTGAAATAA CTCTTAGTAA TAAAACAAAG AAAAGCAAAG

ATCCTGATAT CTTATTTATG CGCTGCCAGT TGAGCCGATT

ACAGAAAGGG CATGCCACAG ATGAATGGTT TCTGCTCAGC

TCCCATATAC CATTAAAAGG TATTGAACCA GGGTCCCTGC

GTGTTCGAGC ACGATACTCT ATGGAAAAAA TCATGCCAGA

AGAAGAGTAC AGTGAATTTA AAGAGCTTAT ACTGCAAAAG

GAACTTCATG TAGTCTATGC TTTATCACAT 3'

6. Identification of GAP DNA Sequences Longer Than GAP 6

General Technique: A novel procedure was used to identify plaques that contain GAP cDNA inserts larger than those present in GAP 6 which consisted of elucidating inserts present in either the λgt11 library described above, or a λgt10 library described below. The procedure consisted of synthesizing cDNA inserts using DNA oligonucleotides having sequences complementary to the 5' region of GAP 6, and oligonucleotide primers that flank the EcoRI insertion sites of λgt11, or λgt10, using the polymerase chain reaction, or PCR. The newly identified PCR products were sequenced, and accordingly DNA probes were synthesized having sequences 5' of GAP 6. These probes were, in turn, used to identify plaques containing larger GAP cDNA inserts. The procedure was repeated several times using as probes, DNA sequences progressively further 5' of GAP 6 identified from each round of newly synthesized cDNA inserts.

PCR is described in U.S. Pat. Nos. 4,683,202 and 4,683,195, both of which are hereby incorporated in their entirety. In general, the synthesis/amplification of DNA sequences by PCR involves an enzymatic chain reaction that produces, in exponential quantities, a specific DNA sequence, provided that the termini of the sequence are known in sufficient detail so that oligonucleotide primers can be synthesized which will hybridize to them, and that a portion of the sequence is available to initiate the chain reaction. One primer is complementary to the negative strand, and the other is complementary to the positive strand. As applied to the instant invention, the primers employed are complementary to the 5' end of GAP 6, and are complementary to and flank the EcoRI sites of λgt11, or λgt10. Because the orientation of a particular cDNA insert in either vector is not known, it was necessary to run separate reactions with oligonucleotides that flank both sides of the EcoRI site. Exemplary of primers usable with λgt11 are two 24-base sequencing primers, 1218 and 1222, produced by New England Biolabs. Similarly, primers compatible with λgt10 are also available from New England Biolabs, and these are 1231 and 1232. Thus, separate reactions were run with either 1218, 1219, or 1231 and 1232, and the appropriate GAP 6 primer.

The primers are annealed to denatured DNA acid, followed by extension with a suitable DNA polymerase enzyme, such as the large fragment of DNA polymerase I (Klenow), or preferably a DNA polymerase that is stable in the presence of detergents and nucleotides, which results in newly synthesized plus and minus strands containing the target sequence. Alternatively, a thermostable enzyme may be used which is present in thermostable bacteria. The enzyme may be produced using DNA recombinant techniques as described in U.S. patent application, Ser. No. 063,509, filed Jul. 17, 1987. Because the newly synthesized sequences are also templates for the primers, repeated cycles of denaturing, primer annealing and extension results in exponential accumulation of the region defined by the primer. PCR thus produces discrete nucleic acid duplexes of cDNA inserts having termini corresponding to the ends of the specific primers employed.

Although PCR can be performed using a variety of reaction conditions, as described in the references presented above, the preferred reaction conditions are as follows. Plaques that hybridize to a particular probe are eluted into either 0.5 ml of water, or SM buffer, and 50 µl of the eluate combined with 10 µl of 10×PCR buffer, 1.5 µl of 10 mM dNTP's, 1 µl of a first and second primer, each at a concentration of about 20 pmoles, 0.2 µl of Taq polymerase equivalent to 1 unit of activity. The final volume is 100 µl. PCR 10×buffer consists of 500 mM KCl, 200 mM Tris-HCl, pH 8.4, 25 mM MgCl$_2$ and 1 mg/ml.

GAP encoding sequences: Gap 6 DNA was sequenced, and an oligonucleotide probe based on the sequence, GW50, synthesized, radiolabelled, and used to rescreen the Clontech λgt11 library, and to screen a second cDNA library made from K562 cells. K562 cDNA was cloned in λgt10, and a description of this library is presented by Mes-Masson et al., 1986, in the PNAS, 83:9768. This publication is hereby incorporated by reference in its entirety. The oligonucleotide, GW50, has the following sequence:

5'TTTAAATTCACTGTACTCTTCTTCTGGCATGAT 3'

Hybridization of GW50 to either library was conducted as described above with the exception that the washing steps after the hybridization were more stringent. Specifically, the filters containing plaques were washed twice, for 15 minutes each wash, with 2×SSC containing 0.1% SDS at room temperature and then two additional washes, for 15 minutes each, with 0.2×SSC containing 0.1% sodium dodecyl sulfate at 55° C. Autoradiography of the filters prepared from the Clontech library revealed 160 positive plaques, while only one plaque was detected from the K562 library.

Using the sequence of GAP 6, DNA primers, LC121 and LC122, with sequences complementary to the 5' region of GAP 6, were synthesized.

LC121 5'GAGGAAGATCATCAAAGACAAACTCT 3'
LC122 5'TCTGTAATCGGCTCAACTGGCAGCG 3'
LC121 corresponds to the 5' end of GAP 6 in the anti-sense direction.

The 163 positive plaques from the Clontech library, and the one positive plaque from the K562 library, were removed from agarose plates using a Pasteur pipette, and eluted into 0.5 ml of SM buffer for 30 minutes. Each isolate was then PCR processed as described above using LC121 in combination with the appropriate λ primers. Typically, a denaturation step was run for 2 minutes at 94° C., followed by an annealing step for 30 seconds at 55° C., and an extension step for 5 minutes at 72° C. The reaction was most often run for 30 cycles. The resulting amplified cDNA inserts were sequenced.

Sequencing can be performed using the techniques referred to above, or by direct sequencing of single stranded DNA produced by PCR. The use of PCR to generate single stranded DNA is described in a co-pending U.S. patent application, Ser. No. 248,896, entitled "Method for Generating Single Stranded DNA by the Polymerase Chain Reaction", filed on Sep. 23, 1988. This patent application is hereby incorporated by reference in its entirety.

Typically about 50 µl of the PCR reaction was separated on a 1% agarose TAE gel, the region of the gel containing the amplified products excised, and the PCR products extracted from the agarose and suspended in about 10 µl–20 µl of TE buffer. Generally about one tenth of this volume was subjected to asymmetric PCR amplification. The reaction conditions employed are described in the above cited patent application. The primers were typically used in a ratio of about 100:1, or about 50:0.5 pmoles.

Using LC121, 14 of the 163 λgt11 plaques were found to have an additional 320, or greater number of base pairs 5' of GAP 6, while the single plaque isolated from the K562 λgt10 library, referred to as K16, was determined to have a cDNA insert consisting of GAP 6 plus an additional 700 base pairs 5' thereto. Based on the latter sequence, several additional oligonucleotides, LC136, LC138, and LC140 were synthesized and used in conjunction with LC121 to again screen the 163 plaques from the Clontech library. The primers have the following sequences:

LC136 5' CGTAAATTGCAAAATGCCTGCAGACCTTG 3'

LC138 5' GTTTTCCTTTGCCCTTTTTCAGAAGATAAC 3'

LC140 5' TGTCATTGAGTACTTGTTCTTGATCCTGC 3'

Rescreening the 163 plaques with LC136 revealed that 82 plaques were positive, while rescreening with LC138 plus LC140, revealed that 63 of the plaques were positive. Of the 63 positive plaques, 38 were subjected to PCR using the primers 1218 and LC138; and 1222 and LC138. Of these, six were found to have long stretches of DNA 5' to GAP 6. Sequencing in M13m18 revealed that they represent different length fragments of the same type of transcript. Two of the clones were studied in detail, clone 7 and clone 101. Clone 101 contained sufficient DNA to encode a protein of 1047 amino acids, which would have a MW of 116,000 daltons. This is similar to the MW of the GAP protein purified from human placenta as described above. Thus, clone 101 contains the full length GAP cDNA. Clone 101 was sequenced, and the sequence is shown in FIGS. 5A–5D. Clone 7 was also sequenced, and shown to have the identical sequence as clone 101 but lacking 33 base pairs from the 5' end.

Figure 6:
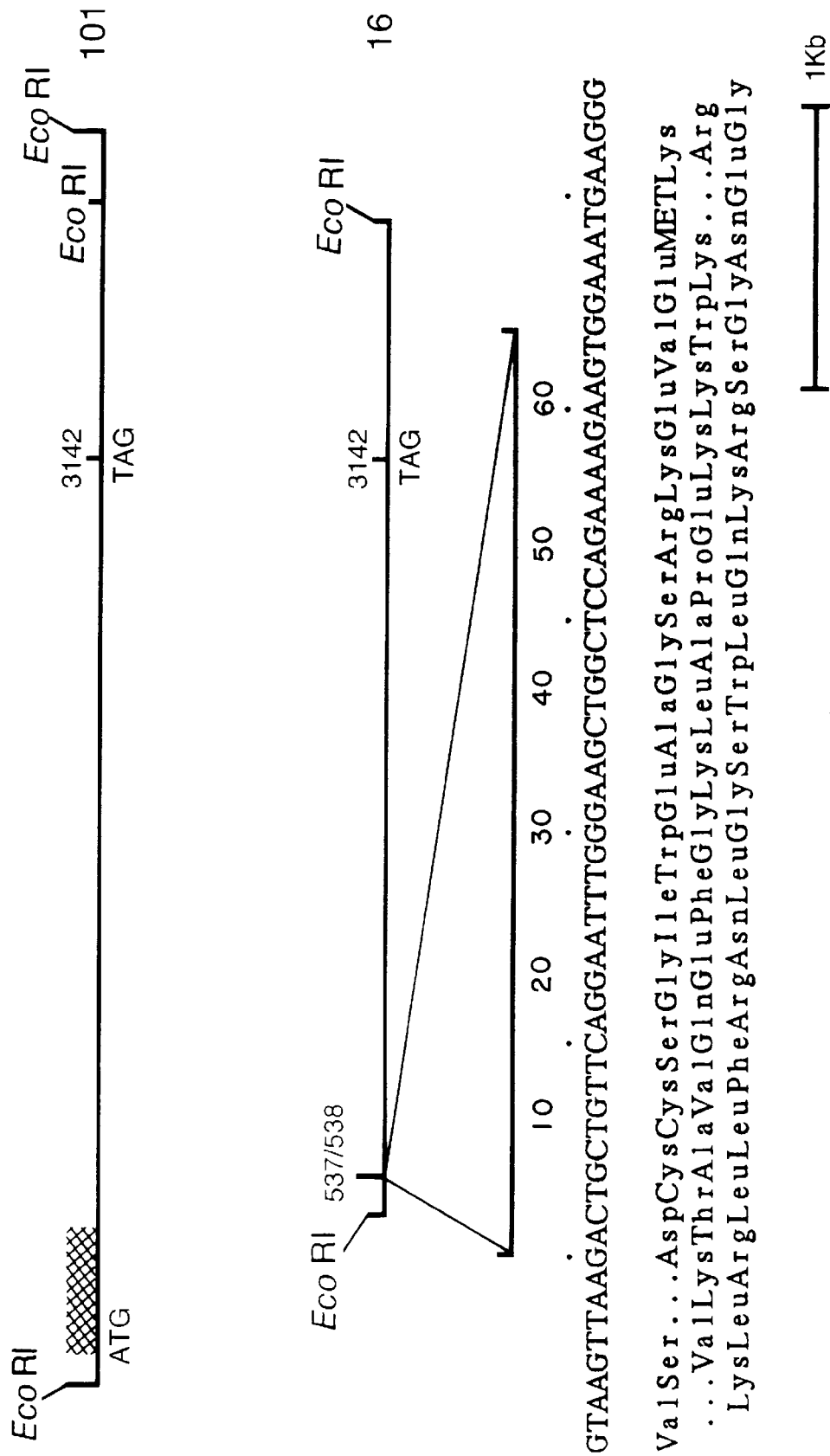
FIG. 6 presents the structural relationship between lambda clones, clone 101 and clone 16.

In addition to the above, two plaques were identified from the 163 plaques initially determined to be positive with GW50 that contained cDNA inserts consisting of an additional 65 base pairs inserted between nucleotides 537 and 538 of clone 101. One of the two clones, clone 16, lacks the first 180 amino acids of clone 101, while the other clone, clone "Sleepy", lacks at least the first 180 amino acids, and additionally has a truncated 3' end at about base 2448 of clone 101. The DNA sequence of the 65 base pair insert is shown in FIG. 6 for clone 16.

7. Expression of GAP

Figure 7A:
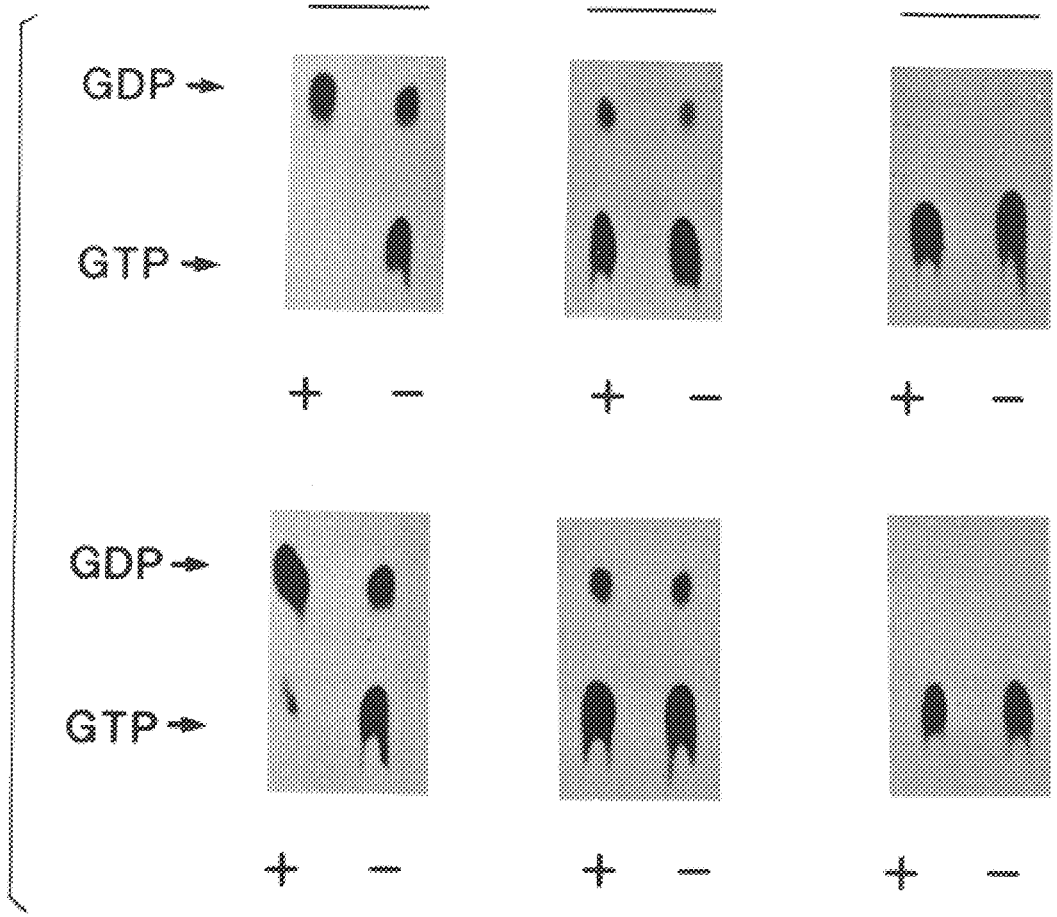
FIG. 7A shows the results of GAP assays conducted in the presence of lysates prepared from λ lysogens of clones 7 (FIG. 7A, top portion) and 101 (FIG. 7A, bottom portion) (top panel)

Lambda lysogens: GAP activity was detected from lysates of λ lysogens of clones 7, 16, and 101. Lysogens were generated in E. coli strain Y1089. The procedures for growing, inducing, harvesting, and lysing the cells is described in T. Huynh et al., in "DNA Cloning Techniques: A Practical Approach", D. Glover, Ed. (IRL Press, Oxford, 1985) pp 49–78. This publication is hereby incorporated by reference in its entirety. Briefly, supernatants obtained from lysates were dialyzed into GAP assay buffer consisting of 20 mM Tris-HCl, pH 7.0, 1 mM MgCl$_2$, 0.1 mM DTT, 0.1% NP40, 100 μM PMSF, and GAP activity measured using the TLC-based GTPase assay described above. 2.2 μM of either normal N-ras p21 protein having glycine at position 12, or mutant p21 proteins wherein glycine is substituted with aspartic acid or valine, were incubated with 0.25 μM [α-$^{32}$P] GTP (800 Ci/mmole) for 15 minutes at 37° C. in the presence or absence of λ lysate. As discussed earlier, the mutant p21 proteins have transforming activity and do not exhibit significant GAP stimulatable GTPase activity. About 10 μl of lysate or GAP assay buffer was added, and after 1 hour at room temperature, p21 was immunoprecipitated and associated nucleotides analyzed by chromatography on PEI cellulose in 1M LiCl. An additional control was run for GAP activity; it consisted of testing an irrelevant lysogen lysate, specifically λgt11 lacking a cDNA insert. The results are shown in FIG. 7A for clones 7 and 101. The upper part of FIG. 7A shows the results for clone 7, while the lower region of FIG. 7A shows the results for clone 101. It is apparent that lysates from both clones stimulate the hydrolysis of GTP to GDP in the presence of normal p21, but not in the presence of mutant p21 proteins. Moreover, when GAP buffer is substituted for normal p$^2$1, or the mutants, there was no effect on GTP hydrolysis. The irrelevant lysogen lysate also did not support GTP hydrolysis.

Transfection of Spodoptera frugiperda: The full length cDNA insert in clone 101 was expressed in insect cells, Spodoptera frugiperda. The insect cell line, Sf9, was transfected with a baculovirus expression vector, pAcC12, containing the GAP encoding EcoRI fragment of clone 101, and GAP activity measured in cell extracts.

Figure 8:
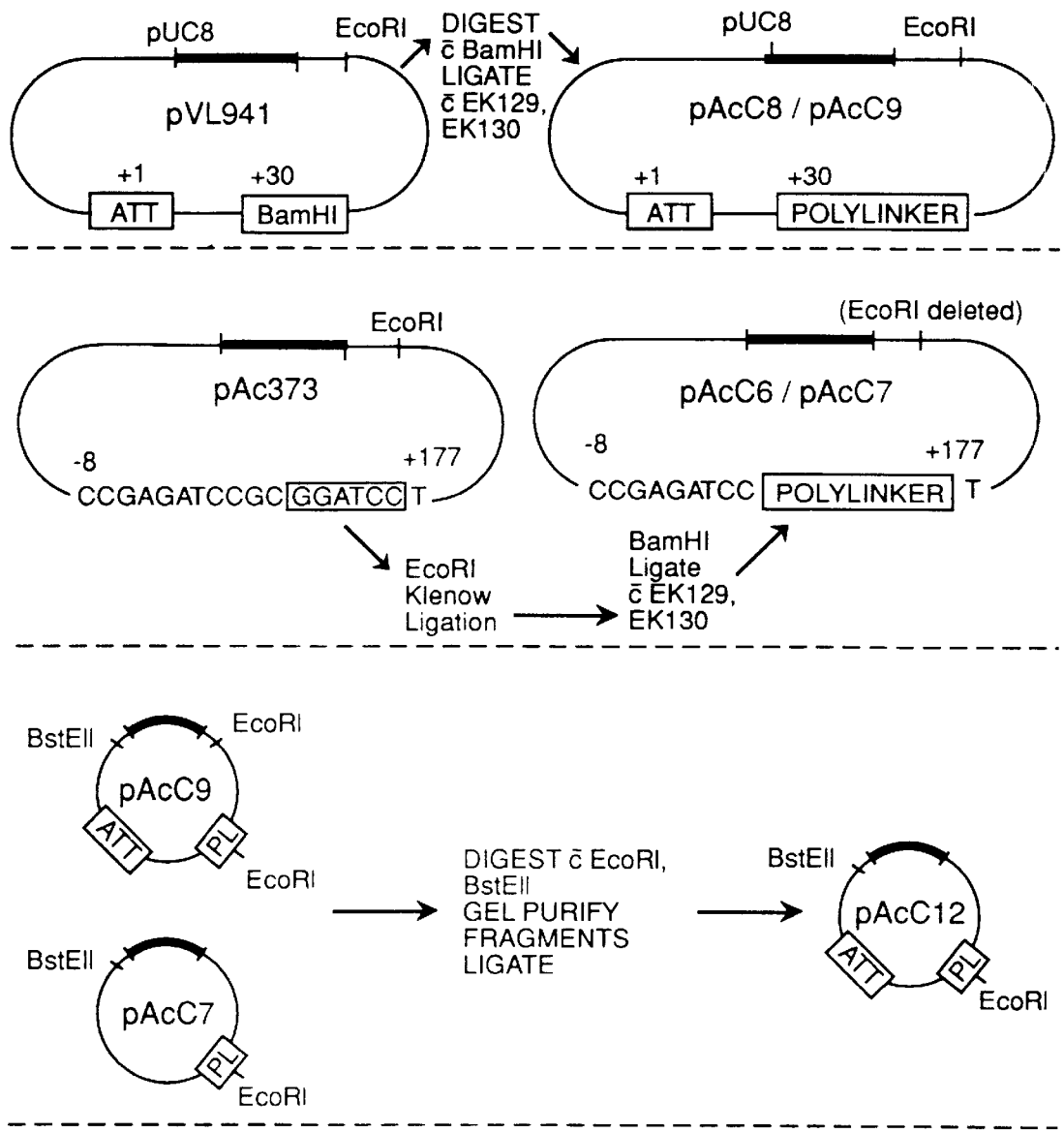
FIG. 8 shows the construction of pAcC12.

The baculovirus vector, pAcC12, was constructed from preexisting vectors, particularly pAc311 and pAc373, as described by Luckow and Summers, 1988, in Biotechnology, 6:47; U.S. Pat. No. 4,745,051; and EPA 127,839. Additional details are presented by Summers and Smith in "A Manual of Methods for Baculovirus Vectors and Insect Cell Culture Procedures", Texas Agricultural Experiment Station Bulletin No. 1555, May, 1987. All of these references are hereby incorporated in their entirety.

pAcC12 was constructed as described below, and as shown in FIG. 8. The transfer vector pAc311 was site-directed mutagenized using M 13 mutagenesis techniques to convert the polyhedron gene initiation codon, ATG, to ATT. The resulting vector was designated pVL941, and is described in detail by Luckow and Summers in Virology, titled "High Level of Expression of Non-Fused Foreign Genes with Autographa Californica Nuclear Polyhedrosis Virus Expression Vectors". A polylinker was inserted into pVL941 at a unique BamHI site 30 base pairs downstream of the ATT sequence. pVL941 was digested with BamHI, and the polylinker, consisting of two complementary self-annealed oligomers, EK 129 and EK130, having the sequences shown below, ligated to produce the vectors pAcC8 and pAcC9 that carry the polylinker in different orientations. The polylinker has a restriction site for EcoRI, as well as for other restriction enzymes.

EK 129:

5'GATCCACCATGGAGCTCGAGATCTAGAATTCTGCAGCCCGGGTACCGATC 3'

EK 130:

5'GATCGGTACCCGGGCTGCAGAATTCTAGATCTCGAGCTCCATGGTGGATC 3'

Because pAcC8 and pAcC9 have two EcoRI restriction sites, one in the polylinker and the other in the plasmid DNA as shown in FIG. 8, it was desirable to remove the plasmid EcoRI site so that the GAP EcoRI encoding fragment of clone 101 could be inserted into the polylinker site. This was achieved using the transfer vector pAc373. pAc373 is similar to pAc311 except that the nucleotide sequences spanning the polyhedron start codon differ. Thus, the EcoRI site was removed from pAc373 by digesting the vector to completion with EcoRI, and the ends made blunt using the Klenow fragment under the appropriate reaction conditions. Following ligation and transformation into *E. coli* DH 5, colonies were identified that lacked the EcoRI site by restriction analysis of miniprep DNA.

pAc373 lacking the EcoRI site was further modified by incorporating the polylinker consisting of the oligomers, EK129 and EK130, shown above, by digesting the vector with BamHI, followed by ligating the oligomers. The resulting vectors, pAcC6 and pAcC7, contain the polylinker in different orientations.

The final construct, pAcC12, was generated from pAcC7 and pAcC9 as shown in FIG. 8. These vectors contain the polylinker in the same orientation. Both vectors were digested with BstEII and EcoRI and the resulting fragments electrophoretically purified. The BstEII/EcoRI fragment of pAcC7 containing the pUC 8 sequences, and partial polylinker sequences was ligated to the large BstEII/EcoRI fragment of pAcC9. This latter fragment contains the ATT sequence and the remaining polylinker sequences.

Figure 7B:
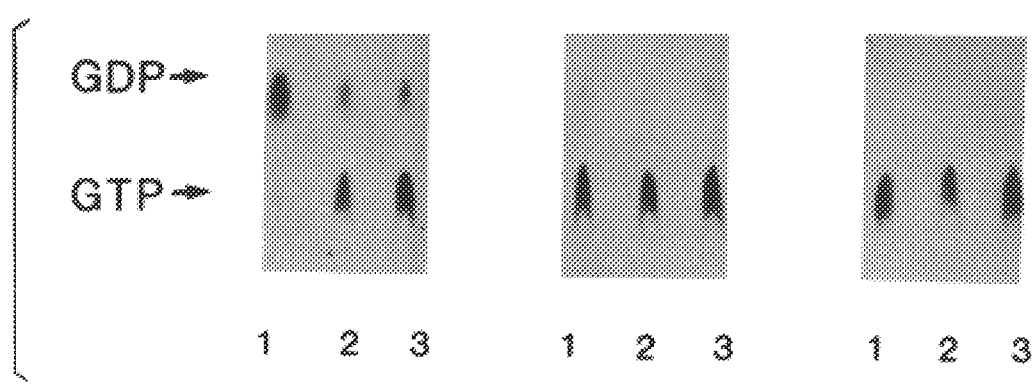
FIG. 7B shows the results of GAP assays conducted in the presence of *Spodoptera friguiperda* (hereinafter referred to as Sf9) cell lysates transfected with pAcC1 2-GAP 5.

The transfer vector, pAcC12, has the EcoRI GAP fragment of clone 101 inserted in both orientations. The correct orientation was designated pAcC12 GAP 5, while the incorrect orientation was designated pAcC12GAP 101-7. About 2 $\mu$g of either plasmid was transfected into $2 \times 10^5$ Sf9 cells, the cells grown for 4 days, isolated by centrifugation, and cell extracts made by solubilizing the cell pellet. The preferred solubilization solution consists of 0.5% NP40, 10 mM Tris HCl, pH 8.0, and 150 mM NaCl. The extract was centrifuged for 15 minutes at 15,000×g and aliquotes diluted into GAP assay buffer, and assayed for GAP activity as described above. Methods for growing Sf9 cells are well known in the art, and detailed procedures for their cultivation can be found in M. Summers and G. Smith in "A Manual of Methods for Baculovirus Vectors and Insect Cell Culture Procedures", Texas Agricultural Experiment Station, Bulletin No. 1555 (May, 1987) or in EPO 127,839 to G. E. Smith and M. D. Summers. Preferred media and culturing conditions can be found in co-pending, commonly owned U.S. patent application, Ser. Nos. 77,181, entitled "Airlift Insect Cell Culture", filed Jul. 24, 1987; 77,303, entitled "Serum Free Media for the Growth of Insect Cells and Expression of Products Thereby", and 77,189, entitled "Lipid Microemulsions for Culture Media". These publications and patent applications are hereby incorporated by reference. FIG. 7B, shows the results. The effect of pAcGAP 5 and pAcGAP 101-7 are shown in lanes 1 and 2, respectively; lane 3 presents a buffer control. Note that pAcGAP 5-stimulates normal ras p21 GTPase activity, whereas it is without effect on the p21 mutants. In contrast, there is no stimulation of GTPase activity by pAcGAP 101-7 of either normal ras p21 or the mutants.

It is important to note that baculovirus can be recovered from Sf9 cells transfected with the above described transfer vectors using the techniques described by Summers and Smith, above. Such virus can be employed to transform cells directly with the appropriate GAP clone.

8. Uses of GAPs

A. Diagnostic Uses of GAP Sequences:

The GAP DNA sequences described herein can be used to produce GAP, which, in turn, can be used to produce antibodies to GAP. These antibodies may be used to isolate GAP using antibody purification techniques generally known in the art. Since GAP is one reagent employed in assaying for the presence of normal ras p21, as described above, especially in tumors thought to result from the over expression of ras p21, and is now available only in limited amounts because of the burdensome purification methods used to obtain it, the availability of large amounts of GAP will be a valuable addition to present cancer diagnostic methods.

The GAP DNA sequences disclosed herein may also be used to determine the number of copies of the GAP gene present per cell in various types of cancers, that is to say, whether the gene is amplified. It is applicant's belief that tumors thought to be causally related to ras expression, over express GAP via gene amplification. Thus, the GAP DNA sequences disclosed herein can be used to measure the degree of over amplification, and diagnostic and prognostic correlations established.

The GAP DNA sequences can be used to measure the level of amplification following techniques generally known in the art. D. Slamon et al, 1987, *Science* 235:177; U.S. Pat. No. 4,542,092 and U.S. Pat. No. 4,699,877; R. Schimke, 1982, *Gene Amplification,* Cold Spring Harbor Laboratory. These publications are hereby incorporated by reference in their entirety. GAP gene amplification can be measured directly using established DNA hybridization techniques. DNA is prepared from human tumor tissue as described by Maniatis et al., and Slamon et al., above, or J. Southern, 1975, *Mol. Biol.* 98:503, and reacted with labeled GAP DNA. GAP 6, GAP 2 or GAP 8 sequences may be used. The entire sequence may be used, or short nucleotide sequences derived therefrom. Normally, a sequence should have at least about 14 nucleotides, and preferably at least about 18 nucleotides. Various labels may be employed to label the GAP sequences, most commonly radionuclides, particularly 32 P are used. However, other techniques may also be employed, such as using biotin modified nucleotides for introduction into a polynucleotide. The biotin then serves as the site for binding to avidin or antibodies, which may be labelled with a wide variety of labels, such as radionuclides, fluorescent molecules, enzymes, or the like. Alternatively, antibodies may be employed which can recognize specific duplexes, including DNA duplexes, RNA duplexes and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected. The DNA probe labelling procedures are known in the art. See, Maniatis et al., above.

A suitable DNA preparation and hybridization procedure to determine the number of GAP genes per cell using dilutional analysis as described by Slamon et al, above, consists of extracting and digesting tumor DNA using the procedure of Maniatis et al., above, followed by subjecting about 10–15 $\mu$g of EcoRI digested DNA to electrophoresis in 0.8% agarose gel, or dilutions of the digested DNA and transferring the DNA onto nylon filter papers. The filters are baked in a vacuum oven for 2 hours at 80° C., prehybridized in 5×SSC solution containing 50% formamide, 10% dextran sulfate, 0.1% SDS, denatured salmon sperm DNA (1 mg/ml), and 4×Denhardt's solution for 12 hours. The DNA can then be hybridized in the same solution containing 32 P-labelled nick-translated GAP 8 probe with a specific activity of about $1 \times 10^8$ cpm/$\mu$g DNA, or about $2 \times 10^6$ cpm/ml. Optimal hybridization and washing conditions can be especially determined, however results may be apparent if hybridization occurs for 48 hours at 42° C., and the filters are washed in succession as follows: 2×SSC for 20 minutes at room temperature; two washes of 30 minutes each in 2×SSC, 0.1% SDS at 65° C.; and one wash of 30 minutes in 0.5×SSC, 0.1% SDS at 65° C. Filters can then be exposed to x-ray film for autoradiography, and the degree of amplification ascertained using established methods, including soft laser densitometry scanning.

Using the above techniques, a correlation may be observed wherein individuals with tumors that have 2–4 copies of GAP enjoy a favorable diagnosis and are unlikely to develop an aggressive malignancy, whereas tumors with 4 or more copies are likely to have aggressive malignancies, and require extensive medical treatment.

In addition to directly detecting GAP gene amplification by the foregoing procedures, amplification may also be detected indirectly by measuring GAP gene messenger RNA levels with labelled GAP DNA sequences. The procedures generally applicable to this method are described in Maniatis et al., above, and in U.S. Pat. No. 4,699,877.

9. Purification Protocols for Native and Recombinant Types I and II GAP:

Two forms of native GAP were purified from human placental tissue. In addition to the 120 kD Type I GAP reported previously (Trahey et al., 1988, supra), an equivalent amount of a 95 kD molecule with GAP activity was recovered and shown to have the N-terminal sequence expected for Type II GAP. The two GAP forms in placental extracts were resolved by molecular sieve chromatography and appeared to have a monomeric native structure.

Type I recombinant GAP was produced intracellularly in Sf9 insect cells using a baculovirus expression vector, and 10-milligram quantities were purified to homogeneity in three steps. Comparison of the purified native and recombinant GAP molecules revealed that all three displayed similar biological specific activities in an in vitro GAP assay. A polyclonal antibody to the purified recombinant GAP was prepared and shown to have a high neutralizing titer against both native and recombinant GAP. The antibody was also highly specific for the detection of native GAP by Western blot. The 95 kD and 120 kD GAP species were detected in approximately equal amounts in fresh placenta, but only the 120 kD form was observed when other human tissues were examined.

Example 2 describes the purification of both Type I and Type II GAP from human placenta and compare these molecules to full-length recombinant Type I GAP purified from insect cells.

Two different MW forms of native GAP were purified from human placenta and were shown to be present in the cytoplasm in approximately equal amounts. The larger MW form has been previously shown to be Type I GAP (Trahey et al., 1988, supra) and represents the predominant GAP species detected in all mammalian tissues that have been examined. A smaller MW form of GAP, which hitherto had not been obtained, was also purified and shown by N-terminal sequence analysis to correspond to Type II GAP. Both GAP species appear to have similar biological activities in an in vitro bioassay for GTPase activation of ras p21. Type II GAP represented approximately 50% of the total GAP recovered from the placenta, but was not expressed in detectable amounts in a number of adult and fetal tissues.

An mRNA coding for Type II GAP was first identified in human placenta (Trahey et al., 1988, supra) and was thought to be derived by a differential slicing event. This patent application teaches that the protein corresponding to this GAP message exists at a high level in the placenta, and that, based on the N-terminal sequence data, initiation of translation does indeed occur at the ATG in the 65 bp mRNA insert, as originally proposed (Trahey et Al, 1988, supra).

Without wishing to be bound by the following postulations, it is postulated that the apparent absence of this form of GAP in other human tissues that contain a significant level of the Type I GAP, suggests that this splicing event may be specific to tissue like placenta and may represent a mechanism for controlling production of Type II GAP. The N-terminal 160 amino acids of GAP appear to compose a hydrophobic domain that may be involved in the association of GAP with the cell membrane. If Type I and Type II GAP molecules are both expressed within the same cell type, the relative amounts of the two species might regulate signal transduction between GAP (or other homologous molecules) and membrane-bound ras or other cytoplasmic factors. In addition, the three additional amino acids present at the amino terminus of Type II GAP could also affect the affinity of GAP for important regulatory or effector proteins in vivo.

Molecular sizing analysis of Types I and II GAP indicated that both forms exist as monomeric proteins in the cell cytoplasm. However, since only the cytoplasmic fraction of the placenta was studied, the existence of membrane-associated forms of GAP in complexes with other proteins is not addressed herein.

Recombinant Type I GAP was produced intracellularly in insect cells to provide sufficient quantities of GAP for biochemical studies and to generate a polyclonal antibody to rGAP. In order to obtain an unproteolyzed GAP preparation, the purification method had to be optimized for the removal and inactivation of contaminating proteases. The purified rGAP that was obtained displayed similar physical properties as native Type I GAP. In addition, this rGAP displayed a specific activity in vitro that was essentially equivalent to that of native GAP on N-ras p21. The specific activity for this purified Type I GAP is apparently about 10-fold higher than that reported for bovine ras GAP (Vogel, et al., 1988, Nature, 335:90). This may be due to differences in the activity of GAP on Ha-ras (used to determine the specific activity of bovine GAP) instead of the N-ras used here, or on the inherent activities of bovine versus human GAP on human ras proteins. Nonetheless, the properties of the human recombinant GAP are similar, if not identical, to human native GAP, thus allowing the use of this recombinant protein for the investigation into the action of GAP in the cell.

10. SDS-PAGE Purification and N-Terminal Amino Acid Analysis:

SDS-PAGE was performed using a modification of the method of Laemmli, 1970, Nature, 227:680, as described below. Preparative isolation of native Type II GAP was performed on a 6% SDS-polyacrylamide gel pre-electrophoresed with 0.1M Tris buffer (pH 8.9) containing 0.1% SDS after loading 15 $\mu$l of Laemmli sample buffer containing 5% beta-mercaptoacetic acid (final pH 6.8). The gel was run for 90 minutes at 40 mAmps. 10 $\mu$g of DEAE-HPLC-purified Type II GAP, prepared in Laemmli sample buffer, was electrophoresed in Laemmli running buffer containing 0.1 mM thioglycolic acid. The gel was then transferred onto a polyvinylidene difluoride (PVDF) membrane (Applied Biosystems, Inc.) prewetted in methanol and then water, using the standard dry blot technique at 150 mAmps for 40 minutes for each 58.8 $cm^2$ of membrane. The GAP protein band was visualized by Coomassie blue staining and subjected to automated sequence analysis using an Applied Biosystems 470A gas-phase sequencer. (Hunkapiller et al., 1983, Methods of Enzymol., 91:399)

11. Western Blot Analysis:

Except for the modifications noted herein, the procedure was as described in Burnette, W. N., 1981, *Anal. Biochem.*, 112:195. Western blots were prepared by electro-blotting SDS-polyacrylamide gels onto nitrocellulose membranes (Bio-Rad), probing with the anti-rGAP antibody (1/1000 dilution) for 4–15 hours, followed with $^{125}$I-protein A (NEN, supra. NEX-146L, 5 µCi/µg) at 0.35 µCi/ml for 1 hour. The Western blots were blocked, washed, and probed at room temperature in 10 mM sodium phosphate buffer (pH 7.4), containing 150 mM NaCl containing 0.1% bovine serum albumin, 0.1% ovalbumin, 0.1% Tween 20, and 0.02% sodium azide.

Human tissues that were examined included 18-week fetal brain, liver, lung, and spleen (obtained from Advanced Bioscience Resources, Inc., Oakland, Calif.). Adult tissues that were examined included male spleen, lung, liver, female brain and uterus (obtained from the International Institute for the Advancement of Medicine, Exton, Pa.). Tissue homogenates were prepared in 10 mM sodium phosphate buffer (pH 7.4) containing 10 mM EDTA, 2 µg/ml leupeptin, and 200 µM PMSF using a glass tissue homogenizer. The homogenates were clarified by centrifugation at 10,000×g for 10 minutes and measured for protein content by the method of Lowry et al., 1951, *J. Biol. Chem.*, 193:265. 20 µg of protein from each cytoplasmic extract was subjected to Western blot analysis. As shown in FIG. 15, as little as 1 ng of GAP was detected on 24hour exposures using this antibody. However, the level of native GAP detected in human cell extracts was approximately 10-fold higher than the limit of detection.

12. Preparation of a Neutralizing Polyclonal Antibody:

Using the purified rGAP preparation described above, a rabbit anti-rGAP antibody was prepared by Berkeley Antibody Co., Inc. (Richmond, Calif.). 500 µg of purified rGAP was mixed with complete Freund's adjuvant and injected into the axial lymph nodes of each of two New Zealand White rabbits. 21 days later, the rabbits were boosted by intramuscular injection of 250 µg of GAP in incomplete Freund's adjuvant. 10 days later, the rabbits were bled from the ear vein, and 20–30 ml of serum was prepared from each. The immunization protocol was continued for 13 months, boosting on day 21 and bleeding on day 31. Serum from bleeds 4–13 of rabbit #2 were pooled and subjected to a 50% ammonium sulfate precipitation. After centrifugation (10,000×g for 10 minutes), the antibody was resuspended in the same volume, dialyzed into phosphate-buffered saline, filter-sterilized and stored at −70° C.

Neutralization experiments were performed by serially diluting the rGAP antibody in phosphate-buffered saline with a constant amount of native or recombinant GAP (15 U/ml), incubating overnight at 4° C., and then assaying the remaining activity in the filter-binding assay. A neutralizing unit is defined as the amount of antibody required to neutralize 50% of the activity of 2 units of GAP.

To determine the neutralizing titer of the anti-rGAP antibody, serial dilutions of the antibody were incubated with a constant amount of native and recombinant GAP overnight and then tested for activity in the $P_i$-release assay. The antibody displayed an equivalent neutralizing titer against all three forms of GAP tested (Types I and II nGAP, and Type I rGAP), while the pre-immune serum had no effect. The titer was 3300 neutralizing units per ml of serum. The antibody was shown to be specific for GAP since it had no effect on the activity of p21 rap GAP, a human protein with functional similarity to ras GAP (Polakis et al., "Purification of a plasma membrane-associated GTPase-activating protein specific for rap1/Krev-1 from HL60 cells", *PNAS (USA)*, in press) or on the intrinsic GTPase activity of p21 ras (Yatani et al, 1990, *Cell*, 61:769).

The following examples are presented to illustrate the invention, and are not to be construed as limiting the scope of the invention.

EXAMPLE 1

Production of rGAP Using a Baculovirus Expression System

Figure 9:
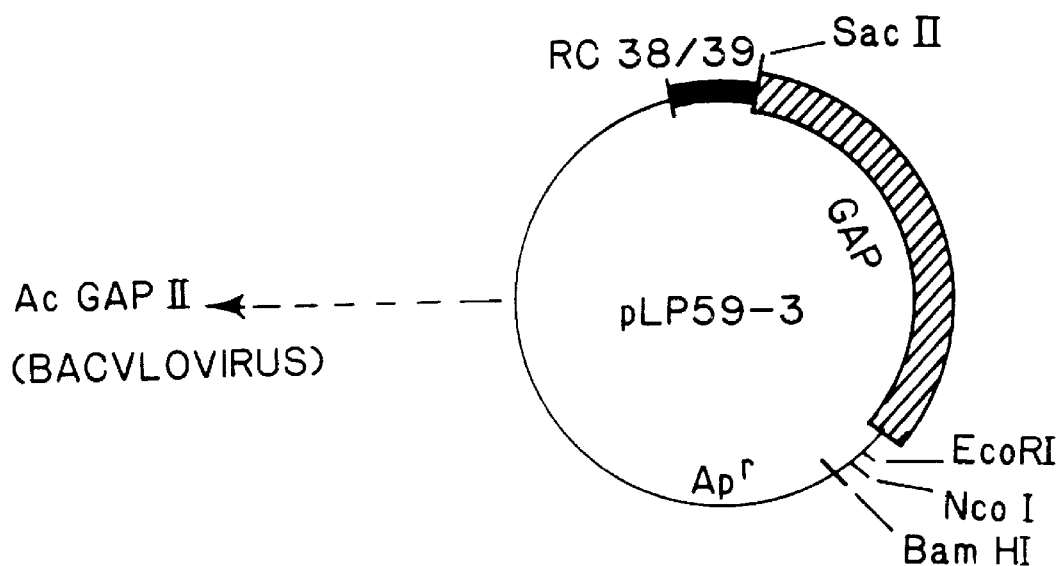
FIG. 9 shows the restriction map of pLP59-3.

Sequence coding for Type I human GAP was recombined into the *Autographa californica* baculovirus (AcNPV) via the transfer vector pLP59-3. The resulting baculovirus is called baculovirus AcGAP 1 1. The AcGAP 11 baculovirus has been deposited with the American Type Culture Collection on Oct. 13, 1989, and has Accession No. VR2255. The transfer vector pLP59-3 was constructed by insertion of a synthetic sequence encoding the first 39 residues of GAP (ATG to SacII) at the NcoI site of pLP31, a derivative of the pAcC3 transfer vector (Devlin, J. J., et al., 1989, *Bio/Tech.*, 7:286; Luckow & Summers, 1988, *Bio/Tech.*, 6:47), followed by insertion of the SacII-BamHI fragment of pGAP-101 (Trahey et al., 1988, supra). This construction places the GAP coding sequence directly adjacent to the polyhedrin untranslated leader sequence and thus eliminates 118 bp of 5' untranslated GAP cDNA. (The restriction map of pLP59-3 is shown in FIG. 9.)

To generate recombinant virus, 2 µg of transfer vector was co-transfected with 1 µg of wild-type viral DNA into Sf9 cells as described by Summers & Smith, 1987, supra. Recombinant virus (occlusion-negative) was isolated from the transfection supernatant by plaque purification (Smith, G. E., et al., 1983, *Mol. Cell Biol.*, 3:2156).

To produce recombinant GAP, Sf9 cells were infected with 5–10 PFU of recombinant virus per cell. Suspension cultures were grown in a stirred bio-reactor sparged with air containing 6 liters of protein-free medium (Maiorella, B., et al, 1988, *Bio/Tech.*, 6:1406). The cells were infected at 1–1.5×10$^6$ cells per ml and were harvested at 48 hour post-infection.

EXAMPLE 2

Purification of Native GAP From Human Placenta

Materials and Methods:

A fresh human placenta was obtained from a full-term delivery by Cesarian section and shown to be negative for HIV and Hepatitis A and B. The placenta was trimmed free of connective tissue, soaked in phosphate buffered saline containing 10 mM EDTA and 1 µg/ml leupeptin (pH 7.4, 4° C.), and then stored in pieces at −70° C. Approximately 300 µg of frozen placenta was thawed in 1.5 liters of 10 mM sodium phosphate buffer (pH 7.4) containing 150 mM sodium chloride, 10 mM EDTA, and 200 µM PMSF (lysate buffer) and then homogenized in a Waring blender. The homogenate was clarified by centrifugation at 10K×g for 15 minutes. Ammonium 30 sulfate was added to 50% saturation, and the solution was held for 1 hour at 4° C. Precipitated protein was recovered by centrifugation at 10K×g for 10 minutes and resuspended in 400 ml of lysate buffer. The crude preparation was dialyzed for 4 hours into 20 mM sodium phosphate buffer (pH 6.5) containing: 5 mM EDTA, 0.1 mM DTT, 1 µg/ml leupeptin and 200 µM PMSF and chromatographed on an S-Sepharose column (5×10 cm, Pharmacia Fast Flow). Proteins were eluted with a 1.5 liter, 0–0.6M sodium chloride gradient. GAP activity eluted as two peaks, as detected using the immunoprecipitation assay. Both peaks of GAP activity were pooled separately (peak I eluted at 170–220 mM, and peak II eluted at 320–400 mM sodium chloride) and dialyzed into 30 mM Tris (pH 8.5) containing 1 mM EDTA, 0.1 mM DTT, 200 μM PMSF, 1 μg/ml leupeptin, and 10% glycerol. The pool of peak I GAP was divided into two portions, and each was subjected to ion exchange chromatography using a TSK-DEAE-5-PW column (21.5×150 mm, BioRad, Richmond, Calif.) eluted with a 0–0.6M sodium chloride gradient The pool of peak II GAP was purified by DEAE-HPLC in a single column run. DEAE column fractions were analyzed for GAP using the non-IP assay and Western blot analysis. The GAP peak I and peak II DEAE pools were dialyzed into 20 mM sodium phosphate buffer (pH 6.5) containing 0.5 mM EDTA, 0.1 mM DTT, 100 μM PMSF, 1 μg/ml leupeptin and 10% glycerol. Each GAP pool was further purified by cation exchange HPLC on a TSK-SP-5-PW column (7.5×75 mm, BioRad) run in the pH 6.5 buffer described above. The GAP was eluted with a 45-min, 0–0.6M sodium chloride gradient (1 ml/min). Tris buffer (1M, pH 8.0) was immediately added to each fraction to raise the pH to 7.5. To obtain a homogeneous GAP II preparation for sequencing, GAP II was purified by SDS-PAGE and transferred onto PVDF, as described above.

Characterization of Native GAP:

The biological activity of the purified Type I GAP was stable for at least 2 weeks at 4° C. The Type II GAP preparation, however, lost activity upon storage. The protein concentration of the purified GAP preparations were determined by the method of Lowry O. H., 1951, *J. Biol. Chem.*, 193:265. Analytical size exclusion-HPLC was performed using a Pharmacia Superose 12 column (1×30 cm, Pharmacia) equilibrated in phosphate buffered saline (pH 7.4) containing 0.1 mM DTT, 0.5 μg/ml leupeptin and 0.1% polyethylene glycol (PEG) 4000 (1 ml/minute).

Results

As described above, native GAP was purified from the cytoplasmic fraction of homogenized human placenta using a four-step procedure involving ammonium sulfate fractionation and a series of ion exchange chromatography steps. The first cation exchange column in the purification resolved GAP into two peaks of activity, as shown in FIGS. 10A–10B.

Western blot analysis of the column fractions was performed using a polyclonal antibody generated against recombinant GAP (described above). FIG. 10B shows two major immunoreactive bands with apparent MW of approximately 120,000 and 95,000 that eluted from the column in regions corresponding to the two GAP activity peaks. The upper band, which had a MW consistent with Type I GAP, eluted first from the column and trailed into the second GAP peak. The lower band, which had a MW consistent with Type II GAP, also eluted broadly but peaked late in the gradient.

Without wishing to be bound by the following, it is postulated that the inability to completely resolve the GAP peaks from one another on this column may reflect structural or other heterogeneity in the two GAP forms. Western blot analysis also revealed several other bands that have a smaller MW than either of the major GAP forms. These may represent proteolytic fragments of GAP peak II, since they appear to co-elute with the second peak of GAP activity.

The fractions enriched for the two GAP forms were pooled and purified separately through DEAE-HPLC and SP-HPLC steps, as described above in *"Materials and Methods"*. In these two subsequent purification steps, GAP peak I resolved as a relatively homogeneous species while GAP peak II appeared to trail on both the DEAE and the SP-HPLC steps.

SDS-PAGE analysis of the purification of both GAP forms is shown in FIG. 11. The purified peak I GAP migrated as a single band at a MW of 120 kD and at a purity of 90% (FIG. 11, lane 5), as determined by scanning densitometry. Peak I GAP migrated at a similar MW under non-reducing conditions (data not shown). The DEAE-purified, peak II GAP preparation consisted of two bands on reducing SDS-PAGE at apparent MW of about 95,000 and 80,000 (FIG. 11, lane 7). To purify the peak II GAP to homogeneity for N-terminal sequence analysis, preparative SDS-PAGE was performed. After electrophoresis, the protein was transferred to a PVDF membrane, visualized by Coomassie-staining, and subjected to N-terminal sequence analysis (described above).

The specific biological activities of the various purified nGAP species are summarized below in Table 1.

TABLE 1

|  | Volume (ml) | Total protein[A] (mg) | Activity[B] (U/ml) | Total activity (units) | Specific activity (U/mg) | Percent Recovered | Fold Purification |
|---|---|---|---|---|---|---|---|
| Placental Cytoplasmic Extract | 1500 | 11,250 | 120 | 180,000 | 15 | 100 | 1 |
| Ammonium Sulfate | 440 | 2,860 | 560 | 245,000 | 85 | 136 | 5 |
| TYPE I GAP | | | | | | | |
| S-Sepharose | 127 | 279 | 830 | 105,400 | 380 | 58 | 24 |
| DEAE-HPLC | 8.7 | 2.8 | 5530 | 48,100 | 17,200 | 27 | 1080 |
| SP-HPLC | 2.0 | 0.28 | 4660 | 9,300 | 33,200 | 5 | 2080 |
| TYPE II GAP | | | | | | | |
| S-Sepharose | 150 | 84 | 780 | 117,000 | 1,390 | 65 | 90 |
| DEAE-HPLC | 4.9 | 2.0 | 4200 | 20,600 | 10,500 | 11 | 660 |

A Protein concentration was determined by the method of Lowry, 1951, supra.
B Units of GAP activity were determined using the $P_i$-release assay with [$\gamma$-$^{32}$P]GTP-bound N-ras p21 as the substrate.

Type I nGAP was purified approximately 2000-fold with an overall yield of 5%. Its biological specific activity was 33,000 U/mg as determined in a $P_i$-release assay using GTP-bound N-ras p21 as the GAP substrate. Type II nGAP was purified approximately 700-fold with an overall yield of 11%. Since the Type II GAP was recovered from the DEAE-HPLC step at a purity of only about 27% (determined by scanning densitometry of a Coomassie-stained SDS-PAGE gel lane), the specific activity of this GAP form was estimated to be approximately 39,000 U/mg, essentially identical to that of Type I GAP.

N-Terminal Sequencing of Native Type II Gap:

The result of the N-terminal sequence analysis of the purified GAP species which had a MW of about 95,000 is shown in FIG. 12. A single sequence was detected. This sequence corresponds to the first 20 amino acids predicted, based on the cDNA, to be at the N-terminus of Type II GAP (Trahey et al., 1988, supra). That is, the first 20 amino acids at the amino-terminus of the native Type II GAP were determined to be:

NH2-Met-Lys-Gly-Trp-Tyr-His-Gly-Lys-Leu-Asp-Arg-Thr-Ile-Ala-Glu-Glu-Arg-Leu-Arg-Gln.

These results establish that translation of Type II GAP initiates near the 3' end of the 65-base-pair insert, beginning with MET LYS GLY, followed by the remaining amino acids as shown above. It is presumed that the remainder of the Type II GAP amino acid sequence is identical, or substantially similar to that of Type I GAP, since the observed MW of the purified Type II GAP corresponds to a protein of that composition.

However, unlike Type II GAP, the N-terminus of Type I GAP is blocked. This was confirmed by subjecting Type I GAP to the preparative SDS-PAGE conditions used to purify Type II GAP and then sequencing its N-terminal amino acids. No sequence was detected under loading conditions similar to that utilized for Type II GAP.

Analysis of Native Types I and II GAP by Molecular Sieve Chromatography:

A freshly prepared placental cytoplasmic extract was subjected to molecular sieve chromatography to determine the native MW of the active GAP species. The results are shown in FIGS. 13A–13B. A broad peak of GAP activity was detected eluting from the column, as shown in FIG. 13A. Analysis of the column fractions by Western blot using the anti-rGAP antibody (FIG. 13B) detected GAP species of two distinct molecular weights, corresponding to Type I and II GAP. The observed native molecular weights are consistent with each type of GAP having primarily a monomeric rather than a multimeric structure.

Western Blot Analysis Using the anti-rGAP Antibody:

The anti-rGAP antibody was tested for its ability to detect rGAP on Western blots (FIG. 15, lanes 1–4). As little as 2 ng of rGAP could be detected on 24-hour film exposures using this antibody. The level of native GAP detected by Western blot analysis of human tissue extracts was about 10fold higher than this limit of detection.

Various human tissues were analyzed by Western blot to characterize the relative distribution of the different GAP species. Purified Types I and II GAP were run as standards for comparison (FIG. 15, lanes 5–6). Analysis of a fresh placental cytoplasmic extract (lane 7) revealed two GAP species having molecular weights equivalent to that of the purified GAP standards. Both GAP bands were present in approximately equal amounts. Although placental tissue contains cells of fetal origin, analysis of cytoplasmic extracts of other human fetal tissues (18-week) revealed only Type I GAP to be present at this stage of development in brain (lane 8), lung (lane 9), liver (lane 10) and spleen (data not shown). Similar results were observed upon analysis of cytoplasmic extracts of the same tissues from adults (data not shown), and from the human breast carcinoma cell line, SKBR-3 (lane 11). Comparison of the relative amount of GAP detected in each lane (20 µg total protein per lane) indicated that placenta had significantly more GAP per microgram of cytoplasmic protein than the other tissues examined.

EXAMPLE 3

Purification of rGAP From Insect Cells

Sf9 insect cells were prepared from two 6-liter culture (described in Example 1 above) and stored as a 85% slurry at −70° C. The paste was thawed in 3 volumes (330 ml) of S-Sepharose Column buffer consisting of 20 mM sodium phosphate buffer (pH 6.5) containing 5 mM EDTA, 0.1 mM dithiothreitol (DTT), 200 µM PMSF, 2 µg/ml leupeptin, and 1 µg/ml pepstatin A. The leupeptin and pepstatin are commercially available from Sigma Chemical Company (P.O. Box 14508, St. Louis, Mo. 63178). The paste was thawed in unchilled buffer at room temperature, which cooled to 4° C. during the process. The resulting mixture was then poured into a pre-rinsed and pre-chilled decompression chamber. Complete cell lysis was achieved by nitrogen cavitation (30 minutes at 250 psi, 4° C.). Alternatively, any form of chemically inert gas can be used in place of nitrogen in the previous step. The crude homogenate was clarified by centrifugation at 10K×g for 10 minutes at 4° C.

To prepare for cation exchange chromatography, the insect homogenate was dialyzed over a 4 hour period into two changes of the S-Sepharose buffer described above. The dialyzed homogenate was recentrifuged (10K×g for 10 minutes), and the supernatant was loaded onto a S-Sepharose column (5×15 cm, Pharmacia Fast Flow) at 8 ml/minute. The column was washed and then eluted with a 1-liter, 0–0.6M sodium chloride gradient. Alternatively, the GAP can be eluted by pH gradient.

Fractions enriched in Type I GAP of MW of about 120,000 were identified by SDS-PAGE analysis and pooled. The rGAP eluted at approximately 200 mM NaCl. The pH of the GAP preparation was adjusted to 8.0 using 1M Tris (pH 8.5) and the protein was then concentrated 7-fold by ultrafiltration using an Amicon YM-10 membrane (final protein concentration 3–4 mg/ml). Alternatively, an ELISA, or an assay based on ras p21 GTPase activation may be used in place of SDS-PAGE analysis identify fractions enriched in GAP.

Size Exclusion Chromatography (SEC) was performed on the eluted protein as follows. The pool of concentrated GAP protein (approx. 50 ml) was divided in half, and each portion was loaded onto a Sephacryl-200 column (Pharmacia 5×90 cm) equilibrated in 50 mM Tris buffer (pH 8.5) containing 100 mM sodium chloride, 1 mM EDTA, 0.1 mM DTT, 200 µM PMSF, 1 µg/ml leupeptin, and 1 µg/ml pepstatin A. Both columns were eluted overnight by gravity flow at approximately 1.5 ml/minute. Fractions containing GAP protein were identified by SDS-PAGE analysis using PhastGel 8-25 (Pharmacia), pooled, and dialyzed into 30 mM Tris (pH 8.5) containing 1 mM EDTA, 0.1 mM DTT, 200 µM PMSF, 1 µg/ml leupeptin, and 1 µg/ml pepstatin A. The dialyzed GAP protein was passed through a 0.45 micron filter and pumped at 3 ml/minute onto a TSK-DEAE-5-PW column (21.5×150 mm, BioRad) equilibrated in the same buffer. The column was washed and then eluted with a 60-minute, 0–0.6M sodium chloride gradient. Recombinant GAP eluted as two major peaks early in the column profile, was identified by SDS-PAGE analysis using PhastGel 8-25 (Pharmacia). Both DEAE pools were individually pooled and dialyzed overnight into 10 mM Tris buffer (pH 7.4) containing 10% glycerol, 1 mM $MgCl_2$, 1 mM EGTA, and 0.1 mM DTT. The recombinant GAP was filter-sterilized and stored at 4° C.

Results

Recombinant GAP was produced in Sf9 insect cells at high levels using the polyhedrin promoter to direct the expression of GAP from the Type I cDNA. Expression levels as high as 10 mg/liter were achieved under optimal growth conditions. Initial attempts to purify rGAP resulted in proteolyzed preparations containing 4 GAP species detected by SDS-PAGE: intact rGAP at MW of about 120,000, two partially proteolyzed GAP species at MW of about 105,000 and 100,000, and a "limit-digest" form of MW of about 95,000 (see FIG. 14, lane 7). Upon further storage at 4° C. the entire preparation was converted into the GAP species of MW of about 95,000 (data not shown). The biological activity of the rGAP remained constant despite the proteolytic degradation. Four preferred measures were subsequently employed to minimize proteolytic degradation: 1) addition of the protease inhibitor, leupeptin, 2) use of $N_2$ cavitation to lyse the cells (rather than freeze/thaw/sonication), 3) minimization of exposure to pHs below 8 at which lysosomal proteases are most active, and 4) inclusion of a molecular sizing chromatography step, which was shown on an analytical scale to remove most of the protease activity.

Using the precautions described above, cell paste from 11 liters of insect culture yielded 22 milligrams of rGAP with an overall recovery of 10% (see Table 2, below). SDS-PAGE analysis of the purification is shown in FIG. 14. The final rGAP preparation was over 90% pure and had a biological specific activity of about 20,000 U/mg. This is within experimental error of the value measured for native Type I GAP protein. The rGAP remained fully active over one year of storage at 4° C.

In the final purification step, preparative DEAE-HPLC, rGAP was resolved into two protein peaks, both of which had essentially equivalent biological specific activities. SDS-PAGE analysis revealed that each peak contained a single band of rGAP protein at the MW corresponding to unproteolyzed MW of about 120,000 rGAP (FIG. 14, lanes 5–6). When the two DEAE peaks were separately dialyzed and re-chromatographed using analytical DEAE-HPLC, they no longer appeared to be different from one another since they eluted with identical retention times. The two GAP species had similar reducing and non-reducing SDS-PAGE molecular weights (data not shown), similar biological specific activities, and similar analytical DEAE-HPLC profiles.

Deposit of Biological Materials:

The following plasmids have been deposited with the American Type Culture Collection on Oct. 11, 1988.

| Designation | ATCC No. | CMCC No. |
|---|---|---|
| pAc GAP 5 (pAcC12 GAP 5) | 67821 | 3437 |
| pGAP 16-4 (Clone 16) | 40503 | 3479 |
| pGAP-SLE1 (Clone Sleepy) | 40504 | 3480 |

Additionally, baculovirus AcGAP 11 which carried the transfer vector, pLP59-3 had been deposited with the American Type Culture Collection (ATCC), 12001 Parklawn Drive, Rockville, Md. 20852 (USA) on Oct. 13, 1989, under ATCC No. VR2255. This deposit had been made pursuant to the provisions of the Budapest Treaty.

Availability of the deposited strains is not to be construed as a license to practice the invention in contravention of the rights granted under the authority of any government in accordance with its patent laws.

Also, the present invention is not to be considered limited in scope by the deposited recombinant transfer vectors, since the deposited vectors are intended only to be illustrative of particular aspects of the invention. Any recombinant baculovirus transfer vector which can be used to prepare recombinant baculoviruses which can function to infect a host insect cell to produce a recombinant protein product is considered to be within the scope of this invention. Further,

TABLE 2

| | Volume (ml) | Total protein[A] (mg) | Activity[B] (U/ml) | Total activity (units) | Specific activity (U/mg) | Percent Recovered | Fold Purification |
|---|---|---|---|---|---|---|---|
| Insect Cell Cytoplasmic Extract | 525 | 1,250 | 4,000 | $21 \times 10^5$ | 1,700 | 100 | 1 |
| S-Sepharose Pool | 118 | 170 | 16,000 | $19 \times 10^5$ | 11,000 | 90 | 6 |
| Sephacryl-200 Pool | 59 | 44 | 16,000 | $9.4 \times 10^5$ | 21,000 | 45 | 12 |
| DEAE-HPLC | | | | | | | |
| (Pool A) | 7.0 | 13.6 | 39,000 | $2.7 \times 10^5$ | 20,000 | 13 | 12 |
| (Pool B) | 5.5 | 8.8 | 32,000 | $1.8 \times 10^5$ | 20,00o | 9 | 12 |
| DEAE-HPLC (Combined) | 12.5 | 22.4 | 35,500 | $4.5 \times 10^5$ | 20,000 | 22 | |

A Protein concentration was determined by the method of Lowry, 1951, supra.
B Units of GAP activity for the DEAE-purified rGAP were determined using the $P_i$-release assay with [$\gamma$-$^{32}$P]GTP-bound N-ras p21 as the substrate. Units of GAP activity for all other samples were determined using the immunoprecipitation method where the purified rGAP was used as a standard with a defined specific activity of 20,000 U/mg. The method used is only accurate within a factor of 2.

various modifications of the invention in addition to those shown and described herein apparent to those skilled in the art from the preceding description are considered to fall within the scope of the appended claims.

Having generally described the invention, it will be appreciated that the scope of the invention is limited only by the appended claims, and not by the particular materials and methods described above.

We claim:

1. A method for obtaining a recombinant guanine triphosphatase activating protein (GAP) from insect cells which express GAP, comprising the steps of:
    a) transforming or infecting insect cells with a vector that encodes GAP or a virus that carries a vector which expresses GAP, respectively;
    b) isolating the transformed or infected insect cells;
    c) lysing the cells;
    d) harvesting the GAP from the cells; and
    e) purifying the harvested GAP by means comprising a cation exchange and a molecular sizing system; wherein the GAP is selected from the group consisting of full length GAPs, muteins of GAPs, fragments of GAPs of about 35 kD or above, and muteins of GAPs of about 35 kD or above.

2. A substantially purified native protein comprising:
    a) an amino-terminal amino acid sequence comprising: NH$_2$-Met-Lys-Gly-Trp-Tyr-His-Gly-Lys-Leu-Asp-Arg-Thr-Ile-Ala-Glu-Glu-Arg-Leu-Arg-Gln;
    b) a molecular weight of about 90–105 kilo-daltons; and
    c) an ability to stimulate GTPase activity of normal ras p21.

3. A substantially pure native Type II GAP.

4. A fragment of Type II GAP comprising an immunogenic activity.

5. A protein comprising an amino-terminal amino acid sequence of: NH$_2$-Met-Lys-Gly, wherein the protein comprises an ability to stimulate GTPase activity of normal ras p21.

6. A protein comprising biological activities of native Type II GAP amino acid sequence, wherein:
    a) the Type II GAP amino acid sequence comprises an amino-terminal amino acid sequence of NH$_2$-Met-Lys-Gly or equivalents thereof; and
    b) the Type II GAP amino acid sequence encodes a polypeptide comprising an ability to stimulate GTPase activity of normal ras p21.

7. A fragment of Type II GAP lacking GAP activity.

* * * * *